(12) United States Patent
Lin et al.

(10) Patent No.: US 8,324,384 B2
(45) Date of Patent: Dec. 4, 2012

(54) GLUCAGON RECEPTOR ANTAGONIST COMPOUNDS, COMPOSITIONS CONTAINING SUCH COMPOUNDS AND METHODS OF USE

(75) Inventors: Songnian Lin, Monroe, NJ (US); Xibin Liao, Edison, NJ (US); Edward Metzger, Somerset, NJ (US); Emma R. Parmee, Scotch Plains, NJ (US); Sheryl D. Debenham, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/148,809

(22) PCT Filed: Feb. 3, 2010

(86) PCT No.: PCT/US2010/022966
§ 371 (c)(1),
(2), (4) Date: Aug. 10, 2011

(87) PCT Pub. No.: WO2010/093535
PCT Pub. Date: Aug. 19, 2010

(65) Prior Publication Data
US 2011/0306624 A1    Dec. 15, 2011

(51) Int. Cl.
| C07D 209/08 | (2006.01) |
| C07D 209/44 | (2006.01) |
| C07D 215/08 | (2006.01) |
| C07D 217/06 | (2006.01) |
| C07D 401/10 | (2006.01) |
| C07D 403/10 | (2006.01) |
| C07D 403/12 | (2006.01) |

(52) U.S. Cl. ........ 544/316; 544/333; 546/146; 546/165; 546/277.1; 548/251; 548/364.7; 548/482; 548/491

(58) Field of Classification Search .............. 544/316, 544/333; 546/146, 165, 277.1; 548/251, 548/364.7, 482, 491
See application file for complete search history.

(56) References Cited

U.S. PATENT DOCUMENTS

| 7,687,534 | B2 * | 3/2010 | Stelmach et al. ............. 514/415 |
| 2004/0122047 | A1 | 6/2004 | Fenton et al. |
| 2005/0272794 | A1 | 12/2005 | Parmee et al. |
| 2006/0084681 | A1 | 4/2006 | Parmee et al. |
| 2007/0088071 | A1 | 4/2007 | Kim et al. |
| 2007/0105930 | A1 | 5/2007 | Parmee et al. |
| 2007/0203186 | A1 | 8/2007 | Beeson et al. |
| 2008/0085926 | A1 | 4/2008 | Stelmach et al. |
| 2008/0108620 | A1 | 5/2008 | Brockunier et al. |
| 2008/0161347 | A1 | 7/2008 | Stelmach et al. |
| 2009/0054506 | A1 | 2/2009 | Liang et al. |
| 2009/0054662 | A1 | 2/2009 | Tan et al. |
| 2009/0105310 | A1 | 4/2009 | Kim et al. |
| 2009/0176854 | A1 | 7/2009 | Parmee et al. |
| 2009/0209564 | A1 | 8/2009 | Kim et al. |
| 2009/0215825 | A1 | 8/2009 | Parmee et al. |
| 2010/0144824 | A1 | 6/2010 | Stelmach et al. |
| 2011/0065634 | A1 | 3/2011 | Greenlee et al. |
| 2011/0172256 | A1 | 7/2011 | Lin et al. |
| 2011/0178007 | A1 | 7/2011 | Stamford et al. |
| 2011/0251248 | A1 | 10/2011 | Lin et al. |
| 2011/0281795 | A1 | 11/2011 | Lin et al. |
| 2011/0301082 | A1 | 12/2011 | Lin et al. |
| 2011/0312911 | A1 | 12/2011 | Kats-Kagan et al. |
| 2012/0010262 | A1 | 1/2012 | Chung et al. |

FOREIGN PATENT DOCUMENTS

| WO | 2010/080971 | 7/2010 |
| WO | 2010/144664 | 12/2010 |
| WO | 2011/037815 | 3/2011 |
| WO | 2011/119541 | 9/2011 |
| WO | 2011/119559 | 9/2011 |

OTHER PUBLICATIONS

Int'l Search Report of PCT/US2010/22966, dated Mar. 22, 2010.

* cited by examiner

*Primary Examiner* — Janet Andres
*Assistant Examiner* — Timothy R Rozof
(74) *Attorney, Agent, or Firm* — Anna L. Cucuzzo; John C. Todaro

(57) ABSTRACT

Glucagon receptor antagonist compounds are disclosed. The compounds are useful for treating type 2 diabetes and related conditions. Pharmaceutical compositions and methods of treatment are also included.

16 Claims, No Drawings

GLUCAGON RECEPTOR ANTAGONIST COMPOUNDS, COMPOSITIONS CONTAINING SUCH COMPOUNDS AND METHODS OF USE

BACKGROUND OF THE INVENTION

The present invention relates to glucagon receptor antagonist compounds, compositions containing such compounds and various methods of treatment relating to type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level >126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure >130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by alpha cells in pancreatic islets in response to falling blood glucose levels. The hormone binds to specific receptors in liver cells that trigger glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Antagonists of the glucagon receptor are useful in improving insulin responsiveness in the liver, decreasing the rate of gluconeogenesis and glycogenolysis, and lowering the rate of hepatic glucose output resulting in a decrease in the levels of plasma glucose.

SUMMARY OF THE INVENTION

The present invention relates to a compound represented by formula I:

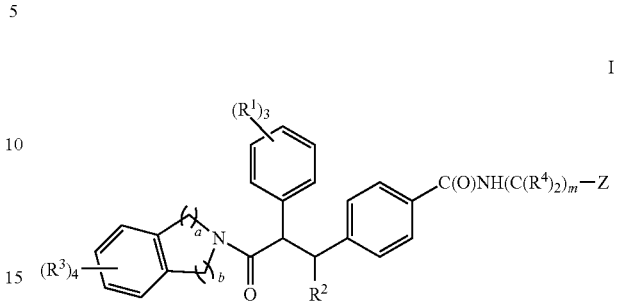

I or a pharmaceutically acceptable salt or solvate thereof wherein:

a is an integer selected from 1, 2 and 3, and b is an integer selected from 0 and 1, such that the sum of a and b is 2 or 3;

each $R^1$ represents H or is selected from the group consisting of: halo, CN, OH, $NO_2$, $CO_2R^a$, $NR^aR^b$, $S(O)_pR^a$, $C_{1-10}$alkyl, $C_{2-10}$alkenyl or $C_{1-10}$alkoxy, the alkyl and alkenyl portions of $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo and $C_{1-6}$alkoxy;

p represents 0, 1 or 2;

each $R^a$ and $R^b$ independently represents H or $C_{1-4}$alkyl optionally substituted with 1-5 halo atoms up to perhalo; and further optionally substituted with 1 group selected from OH, oxo and $C_{1-6}$alkoxy;

$R^2$ represents $C_{1-6}$alkyl or $C_{2-6}$alkenyl, each optionally substituted with 1-5 halo atoms up to perhalo, and further optionally substituted with 1 group selected from OH, oxo and $C_{1-6}$alkoxy;

each $R^3$ represents H or halo, or 1-3 $R^3$ groups represent H or halo and the remainder represent a member selected from the group consisting of: CN; OH; $NO_2$; $CO_2R^a$; $NR^aR^b$; $S(O)_pR^a$; phenyl or 5-6 membered heteroaryl containing 1-3 nitrogen atoms and 0-1 oxygen or sulfur atom, said phenyl and heteroaryl being optionally substituted with 1-3 halo atoms and 1-2 members selected from the group consisting of: $C_{1-3}$alkyl, $C_{1-3}$alkoxy, halo$C_{1-3}$alkyl and halo$C_{1-3}$alkoxy; $C_{1-10}$alkyl; $C_{2-10}$alkenyl and $C_{1-10}$alkoxy, the alkyl and alkenyl portions of $C_{1-10}$alkyl, $C_{2-10}$alkenyl and $C_{1-10}$alkoxy being optionally substituted with 1-5 halo atoms up to perhalo; and further optionally substituted with 1 group selected from OH, oxo, $NR^aR^b$, and $C_{1-6}$alkoxy;

each $R^4$ independently represents H or is selected from the group consisting of: halo, OH, $C_{1-4}$alkyl, $OC_{1-4}$alkyl, halo$C_{1-4}$alkyl and haloO$C_{1-4}$alkyl;

m represents 0, 1 or 2; when m represents 0, Z represents tetrazolyl; when m represents 1, Z represents a member selected from the group consisting of: $CO_2H$, $SO_3H$, $C(O)NH_2$ and tetrazolyl; and when m represents 2, Z represents a member selected from the group consisting of $CO_2H$, $SO_3H$ and $C(O)NH_2$.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like. Cycloalkenyl is a subset of alkenyl. If no number is specified, 4-8 carbon atoms are included. Examples include cyclopentenyl, cyclohexenyl and the like.

"Aryl" (Ar) means mono- and bicyclic aromatic rings containing 6-12 carbon atoms. Examples of aryl include phenyl, naphthyl, indanyl and the like. "Aryl" also includes monocyclic rings fused to an aryl group. Examples include tetrahydronaphthyl, indanyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Halogen" (Halo) includes fluorine, chlorine, bromine and iodine. The terms "haloalkyl", "haloalkoxy" and the like refer to halogenated alkyl and alkoxy groups of the size specified, substituted with 1-5 halo atoms, up to perhalo, and preferably from 1-3 halo atoms selected from fluoro and chloro. For example, haloC$_{1-6}$alkyl refers to a C$_{1-6}$alkyl group substituted with 1 to 5 halo atoms, up to perhalo.

One aspect of the invention that is of interest relates to a compound represented by formula I:

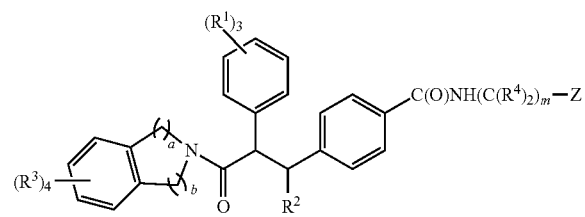

I or a pharmaceutically acceptable salt or solvate thereof wherein:

a is an integer selected from 1, 2 and 3, and b is an integer selected from 0 and 1, such that the sum of a and b is 2 or 3;

each R$^1$ represents H or is selected from the group consisting of: halo, CN, OH, NO$_2$, CO$_2$R$^a$, NR$^a$R$^b$, S(O)$_p$R$^a$, C$_{1-10}$alkyl, C$_{2-10}$alkenyl or C$_{1-10}$alkoxy, the alkyl and alkenyl portions of C$_{1-10}$alkyl, C$_{2-10}$alkenyl and C$_{1-10}$alkoxy being optionally substituted with 1-5 halo atoms up to perhalo; and further optionally substituted with 1 group selected from OH, oxo and C$_{1-6}$alkoxy;

p represents 0, 1 or 2;

each R$^a$ and R$^b$ independently represents H or C$_{1-4}$alkyl optionally substituted with 1-5 halo atoms up to perhalo; and further optionally substituted with 1 group selected from OH, oxo and C$_{1-6}$alkoxy;

R$^2$ represents C$_{1-6}$alkyl or C$_{2-6}$alkenyl, each optionally substituted with 1-5 halo atoms up to perhalo, and further optionally substituted with 1 group selected from OH, oxo and C$_{1-6}$alkoxy;

each R$^3$ represents H or halo, or 1-3 R$^3$ groups represent H or halo and the remainder represent a member selected from the group consisting of: CN; OH; NO$_2$; CO$_2$R$^a$; NR$^a$R$^b$; S(O)$_p$R$^a$; phenyl or 5-6 membered heteroaryl containing 1-3 nitrogen atoms and 0-1 oxygen or sulfur atom, said phenyl and heteroaryl being optionally substituted with 1-3 halo atoms and 1-2 members selected from the group consisting of: C$_{1-3}$alkyl, C$_{1-3}$alkoxy, haloC$_{1-3}$alkyl and haloC$_{1-3}$alkoxy; C$_{1-10}$alkyl; C$_{2-10}$alkenyl and C$_{1-10}$alkoxy, the alkyl and alkenyl portions of C$_{1-10}$alkyl, C$_{2-10}$alkenyl and C$_{1-10}$alkoxy being optionally substituted with 1-5 halo atoms up to perhalo; and further optionally substituted with 1 group selected from OH, oxo, NR$^a$R$^b$, and C$_{1-6}$alkoxy;

each R$^4$ independently represents H or is selected from the group consisting of: halo, OH, C$_{1-4}$alkyl, OC$_{1-4}$alkyl, haloC$_{1-4}$alkyl and haloOC$_{1-4}$alkyl;

m represents 0, 1 or 2; when m represents 0, Z represents tetrazolyl; when m represents 1, Z represents a member selected from the group consisting of: CO$_2$H, SO$_3$H, C(O)NH$_2$ and tetrazolyl; and when m represents 2, Z represents a member selected from the group consisting of: CO$_2$H, SO$_3$H and C(O)NH$_2$.

Another aspect of the invention that is of interest relates to compounds in accordance with formula I or a pharmaceutically acceptable salt or solvate thereof wherein a and b each represent 1, such that the sum of a and b is 2.

Another aspect of the invention that is of interest relates to compounds in accordance with formula I or a pharmaceutically acceptable salt or solvate thereof wherein a represents 2 and b represents 0 such that the sum of a and b is 2.

Another aspect of the invention that is of interest relates to compounds in accordance with formula I or a pharmaceutically acceptable salt or solvate thereof wherein a represents 3 and b represents 0 such that the sum of a and b is 3.

Another aspect of the invention that is of interest relates to compounds in accordance with formula I or a pharmaceutically acceptable salt or solvate thereof wherein a represents 2 and b represents 1 such that the sum of a and b is 3.

Another aspect of the invention that is of interest relates to compounds in accordance with formula I or a pharmaceutically acceptable salt or solvate thereof wherein each R$^1$ represents H or is selected from the group consisting of: halo, CN, C$_{1-6}$alkyl, C$_{1-6}$alkoxy, haloC$_{1-6}$alkyl and haloC$_{1-6}$alkoxy.

In particular, another aspect of the invention that is of interest relates to compounds in accordance with formula I or a pharmaceutically acceptable salt or solvate thereof wherein each R$^1$ represents H or is selected from the group consisting of: halo selected from fluoro and chloro; CN; CH$_3$; OCH$_3$; CF$_3$ and OCF$_3$.

Even more particularly, another aspect of the invention that is of interest relates to compounds in accordance with formula I or a pharmaceutically acceptable salt or solvate thereof wherein each R$^1$ represents H, halo selected from fluoro and chloro; CN; CH$_3$; or CF$_3$.

Another aspect of the invention that is of interest relates to compounds in accordance with formula I or a pharmaceutically acceptable salt or solvate thereof wherein $R^2$ represents a member selected from the group consisting of: $C_{1-6}$alkyl and $C_{3-4}$alkenyl, each optionally substituted with 1-3 halo atoms.

In particular, another aspect of the invention that is of interest relates to compounds in accordance with formula I or a pharmaceutically acceptable salt or solvate thereof wherein $R^2$ represents $C_{2-5}$alkyl optionally substituted with 1-3 halo atoms.

Even more particularly, another aspect of the invention that is of interest relates to compounds in accordance with formula I or a pharmaceutically acceptable salt or solvate thereof wherein $R^2$ represents n-propyl, optionally substituted with 1-3 halo atoms selected from fluoro and chloro.

Another aspect of the invention that is of interest relates to compounds in accordance with formula I or a pharmaceutically acceptable salt or solvate thereof wherein each $R^3$ represents H or halo, or 1-3 $R^3$ groups represent H or halo and the remainder represent a member selected from the group consisting of: CN; OH; $CO_2R^a$; $NR^aR^b$; $S(O)_pR^a$; phenyl or 5-6 membered heteroaryl containing 1-2 nitrogen atoms, said phenyl and heteroaryl being optionally substituted with 1-3 halo atoms and 1-2 members selected from the group consisting of: $C_{1-3}$alkyl, $C_{1-3}$alkoxy, halo$C_{1-3}$alkyl and halo$C_{1-3}$alkoxy; $C_{1-6}$alkyl and $C_{1-6}$alkoxy, the alkyl portions of $C_{1-6}$alkyl and $C_{1-6}$alkoxy being optionally substituted with 1-5 halo atoms up to perhalo.

In particular, another aspect of the invention that is of interest relates to compounds in accordance with formula I or a pharmaceutically acceptable salt or solvate thereof wherein each $R^3$ represents H or halo selected from fluoro, chloro and bromo, or 1-3 $R^3$ groups represent H or halo selected from fluoro, chloro and bromo, and the remainder represent a member selected from the group consisting of CN; $S(O)_pR^a$; phenyl or 5-6 membered heteroaryl selected from the group consisting of: pyrazolyl, imidazolyl, pyridyl, pyrimidinyl and pyrazinyl, said phenyl and heteroaryl being optionally substituted with 1-3 fluoro or chloro atoms and 1-2 members selected from the group consisting of $C_{1-3}$alkyl, $C_{1-3}$alkoxy, halo$C_{1-3}$alkyl and halo$C_{1-3}$alkoxy; $C_{1-3}$alkyl, and $C_{1-3}$alkoxy, the alkyl portions of $C_{1-3}$alkyl and $C_{1-3}$alkoxy being optionally substituted with 1-3 fluoro or chloro atoms.

Another aspect of the invention that is of interest relates to compounds in accordance with formula I or a pharmaceutically acceptable salt or solvate thereof wherein each $R^4$ represents H, halo selected from F and Cl, OH, $C_{1-2}$alkyl, $C_{1-2}$alkoxy, halo$C_{1-2}$alkyl and halo$C_{1-2}$alkoxy wherein the halo portion of halo$C_{1-2}$alkyl and halo$C_{1-2}$alkoxy is selected from F and Cl.

In particular, another aspect of the invention that is of interest relates to compounds in accordance with formula I or a pharmaceutically acceptable salt or solvate thereof wherein each $R^4$ represents H, F, Cl, OH and $CH_3$.

More particularly, another aspect of the invention that is of interest relates to compounds in accordance with formula I or a pharmaceutically acceptable salt or solvate thereof wherein each $R^4$ represents H, F, $CH_3$ or OH.

Another aspect of the invention that is of interest relates to compounds in accordance with formula I or a pharmaceutically acceptable salt or solvate thereof wherein m represents 0 or 1 and Z represents tetrazolyl.

Another aspect of the invention that is of interest relates to compounds in accordance with formula I or a pharmaceutically acceptable salt or solvate thereof wherein m is 1 or 2 and Z represents $CO_2H$, $SO_3H$ or $C(O)NH_2$.

Another aspect of the invention that is of interest relates to compounds in accordance with formula I or a pharmaceutically acceptable salt or solvate thereof wherein m is 2 and Z represents $CO_2H$.

One aspect of the invention that is of particular interest relates to a compound represented by formula I:

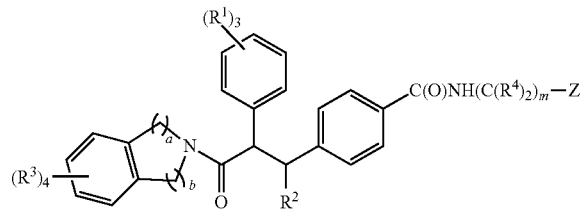

or a pharmaceutically acceptable salt or solvate thereof wherein:

a represents 1 or 2, and b represents 1, such that the sum of a and b is 2 or 3;

each $R^1$ represents H or is selected from the group consisting of: halo, CN, $C_{1-6}$alkyl, $C_{1-6}$alkoxy, halo$C_{1-6}$alkyl and halo$C_{1-6}$alkoxy;

$R^2$ represents a member selected from the group consisting of: $C_{1-6}$alkyl and $C_{3-4}$alkenyl, each optionally substituted with 1-3 halo atoms;

each $R^3$ represents H or halo, or 1-3 $R^3$ groups represent H or halo and the remainder represent a member selected from the group consisting of: CN; OH; $CO_2R^a$; $NR^aR^b$; $S(O)_pR^a$; phenyl or 5-6 membered heteroaryl containing 1-2 nitrogen atoms, said phenyl and heteroaryl being optionally substituted with 1-3 halo atoms and 1-2 members selected from the group consisting of: $C_{1-3}$alkyl, $C_{1-3}$alkoxy, halo$C_{1-3}$alkyl and halo$C_{1-3}$alkoxy; $C_{1-6}$alkyl, and $C_{1-6}$alkoxy, the alkyl portions of $C_{1-6}$alkyl and $C_{1-6}$alkoxy being optionally substituted with 1-5 halo atoms up to perhalo;

each $R^4$ represents H, halo selected from F and Cl, OH, $C_{1-2}$alkyl, $C_{1-2}$alkoxy, halo$C_{1-2}$alkyl and halo$C_{1-2}$alkoxy wherein the halo portion of halo$C_{1-2}$alkyl and halo$C_{1-2}$alkoxy is selected from F and Cl;

m represents 0 or 1 and Z represents tetrazolyl, or m is 1 or 2 and Z represents $CO_2H$, $SO_3H$ or $C(O)NH_2$.

Examples of compounds that fall within the invention described herein are in the tables and examples contained herein. Pharmaceutically acceptable salts and solvates of the compounds disclosed in the tables are included as well.

Another aspect of the invention that is of interest relates to a pharmaceutical composition comprising a compound as described above with respect to formula I or a pharmaceutically acceptable salt or solvate thereof in combination with a pharmaceutically acceptable carrier.

Another aspect of the invention that is of interest relates to a method of treating type 2 diabetes mellitus in a mammalian patient in need of such treatment comprising administering to said patient a compound as described above with respect to formula I or a pharmaceutically acceptable salt or solvate thereof in an amount that is effective to treat type 2 diabetes mellitus.

Another aspect of the invention that is of interest relates to a method of delaying the onset of type 2 diabetes mellitus in a mammalian patient in need thereof comprising administering to the patient a compound as described above in accordance with formula I or a pharmaceutically acceptable salt or solvate thereof in an amount that is effective to delay the onset of type 2 diabetes mellitus.

Another aspect of the invention that is of interest relates to a method of treating hyperglycemia, diabetes or insulin resistance in a mammalian patient in need of such treatment which comprises administering to said patient a compound as described above in accordance with formula I or a pharmaceutically acceptable salt or solvate thereof in an amount that is effective to treat hyperglycemia, diabetes or insulin resistance.

Another aspect of the invention that is of interest relates to a method of treating non-insulin dependent diabetes mellitus in a mammalian patient in need of such treatment comprising administering to the patient an anti-diabetic effective amount of a compound in accordance with formula I or a pharmaceutically acceptable salt or solvate thereof as described above.

Another aspect of the invention that is of interest relates to a method of treating obesity in a mammalian patient in need of such treatment comprising administering to said patient a compound in accordance with formula I as described above or a pharmaceutically acceptable salt or solvate thereof in an amount that is effective to treat obesity.

Another aspect of the invention that is of interest relates to a method of treating Syndrome X in a mammalian patient in need of such treatment, comprising administering to said patient a compound in accordance with formula I as described above or a pharmaceutically acceptable salt or solvate thereof in an amount that is effective to treat Syndrome X.

Another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound as described above with respect to formula I or a pharmaceutically acceptable salt or solvate thereof in an amount that is effective to treat said lipid disorder.

Another aspect of the invention that is of interest relates to a method of treating atherosclerosis in a mammalian patient in need of such treatment, comprising administering to said patient a compound in accordance with formula I as described above or a pharmaceutically acceptable salt or solvate thereof in an amount effective to treat atherosclerosis.

Another aspect of the invention that is of interest relates to a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I as described above or a pharmaceutically acceptable salt or solvate thereof in an amount that is effective to treat said condition.

Another aspect of the invention that is of interest relates to a method of delaying the onset of a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with formula I as described above or a pharmaceutically acceptable salt or solvate thereof in an amount that is effective to delay the onset of said condition.

Another aspect of the invention that is of interest relates to a method of reducing the risk of developing a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I as described above or a pharmaceutically acceptable salt or solvate thereof in an amount that is effective to reduce the risk of developing said condition.

Another aspect of the invention that is of interest relates to a method of treating a condition selected from the group consisting of:

(1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (1.3) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient effective amounts of a compound of formula I as described above, or a pharmaceutically acceptable salt or solvate thereof, and another compound that is selected from the list provided below.

(1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS- 196085, BRL-35135A, CGP12177A, BTA-243, Trecadrine, Zeneca D7114, SR 59119A, and such as those disclosed in U.S. Pat. Nos. 5,705,515, and 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), cetilistat, Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004-139909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II, CHIR86036 (Chiron), ME-10142, and ME-10145 (Melacure), CHIR86036 (Chiron); PT-141, and PT-14 (Palatin); (15) other MC4R (melanocortin 4 receptor) agonists, such as those disclosed in: U.S. Pat. Nos. 6,410,548; 6,294,534; 6,350,760; 6,458,790; 6,472,398; 6,376,509; and 6,818,658; US Patent Publication No. US2002/0137664; US2003/0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869; WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-1 agonists (cholecystokinin-A) agonists, such as AR-R 15849, GI 181771, JMV-180, A-71378, A-71623 and SR146131, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm.(Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) other BRS3 (bombesin receptor subtype 3) agonists such as [D-Phe6,beta-Ala11,Phe13,Nle14]Bn(6-14) and [D-Phe6, Phe13]Bn(6-13)propylamide, and those compounds disclosed in Pept. Sci. 2002 August; 8(8): 461-75); (33) CNTF (Ciliary neurotrophic factors), such as GI-181771 (GlaxoSmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application. Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444 and sitagliptin; and the compounds disclosed in U.S. Pat. No. 6,699,871, which is incorporated herein by reference; and International Patent Application Nos. WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (45) dicarboxylate transporter inhibitors; (46) glucose transporter inhibitors; (47) phosphate transporter inhibitors; (48) Metformin (Glucophage®); (49) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. Nos. 5,026,685, 5,604,203, 5,574,010, 5,696,093, 5,936,092, 6,046,162, 6,046,167, 6,093,692, 6,225,445, 5,604,203, 4,002,531, 4,179,337, 5,122,614, 5,349,052, 5,552,520, 6,127,355, WO 95/06058, WO 98/32466, WO 03/026591, WO 03/057235, WO 03/027637, and WO 2004/066966; (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (53) cyclooxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (54) Neuropeptide Y1 (NPY1) antagonists such as BIBP3226, J-115814, BIBO 3304, LY-357897, CP-671906, GI-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (55) Opioid antagonists such as nalmefene (Revex®), 3-methoxynaltrexone, naloxone, naltrexone, and those disclosed in: PCT Application No. WO 00/21509; (57) 11β HSD-1 (11-beta hydroxy steroid dehydrogenase type 1) inhibitors such as BVT 3498, BVT 2733, and those disclosed in WO 01/90091, WO 01/90090, WO 01/90092, and U.S. Pat. No. 6,730,690 and US Publication No. US 2004-0133011, which are incorporated by reference herein in their entirety; (56) aminorex; (57) amphechloral; (58) amphetamine; (59) benzphetamine; (60) chlorphentermine; (61) clobenzorex; (62) cloforex; (63) clominorex; (64) clortermine; (65) cyclexedrine; (66) dextroamphetamine; (67) diphemethoxidine, (68) N-ethylamphetamine; (69) fenbutrazate; (70) fenisorex; (71) fenproporex; (72) fludorex; (73) fluminorex; (74) furfurylmethylamphetamine; (75) levamfetamine; (76) levophacetoperane; (77) mefenorex; (78) metamfepramone; (79) methamphetamine; (80) norpseudoephedrine; (81) pentorex; (82) phendimetrazine; (83) phenmetrazine; (84) picilorex; (85) phytopharm 57; (86) zonisamide, (87) neuromedin U and analogs or derivatives thereof, (88) oxyntomodulin and analogs or derivatives thereof, (89) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; (90) Qnexa; (91) smoking cessation agents, such as nicotine agonists, partial nicotine agonists, such as vareni-cline, monoamine oxidase inhibitors (MAOIs), antidepressants such as bupropion, doxepine, and nortriptyline; and anxiolytic agents such as buspirone or clonidine.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3 -cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl){3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl){3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl]benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl)methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4- cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5 -fluorobenzonitrile, 3-[(1S)-1-(1-{(S)-(4-chlorophenyl)[3-(1,3,4-oxadiazol-2-yl)phenyl]methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b]pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H), 4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H), 1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro[7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-N-[1-(2-fluorophenyl)-3-pyrazolyl]-3-oxospiro[6-azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide, trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro[chroman-2,4'-piperidin]-4-one; and pharmaceutically acceptable salts and esters thereof. Specific MCH1R antagonist compounds of use in combination with a compound of the persent invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2- methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H -imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H -imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methylpropane-nitrile; and pharmaceutically acceptable salts thereof. Still further, neurokinin-1 (NK-1) receptor antagonists may be favorably employed in combination with a compound of the present invention. NK-1 receptor antagonists of use in the present invention are fully described in the art. Specific neurokinin-1 receptor antagonists of use in the present invention include: (±)-(2R3R,2S3S)-N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; RO67319; R1124; R1204; SSR146977; SSR240600; T-2328; and T2763.; or a pharmaceutically acceptable salts thereof. Examples of other anti-obesity agents that can be employed in combination with a compound of formula I are disclosed in "Patent focus on new anti-obesity agents," *Exp. Opin. Ther. Patents*, 10: 819-831 (2000); "Novel anti-obesity drugs," *Exp. Opin. Invest. Drugs*, 9: 1317-1326 (2000); and "Recent advances in feeding suppressing agents: potential therapeutic strategy for the treatment of obesity, *Exp. Opin. Ther. Patents*, 11: 1677-1692 (2001). The role of neuropeptide Y in obesity is discussed in *Exp. Opin. Invest. Drugs*, 9: 1327-1346 (2000). Cannabinoid receptor ligands are discussed in *Exp. Opin. Invest. Drugs*, 9: 1553-1571 (2000).

Another aspect of the invention that is of interest relates to a method of treating a condition selected from the group consisting of: hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor wherein the HMG-CoA reductase inhibitor is a statin.

Even more particularly, another aspect of the invention that is of interest relates to a method of treating a condition selected from the group consisting of: hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor, wherein the HMG CoA reductase inhibitor is a statin selected from the group consisting of: lovastatin, simvastatin, pravastatin, fluvastatin, atorvastatin, itavastatin, rosuvastatin and rivastatin.

Another aspect of the invention that is of interest relates to a method of reducing the risk of developing a condition selected from the group consisting of: hypercholesterolemia, atherosclerosis, low HDL levels, high LDL levels, hyperlipidemia, hypertriglyceridemia and dyslipidemia, and the sequelae of such conditions, delaying the onset or reducing the risk of developing said condition, comprising administering to a mammalian patient in need of such treatment therapeutically effective amounts of a compound of formula I as described above and an HMG-CoA reductase inhibitor.

More particularly, another aspect of the invention that is of interest relates to a method for delaying the onset of, or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin, and even more particularly, a statin selected from the group consisting of: lovastatin, simvastatin, pravastatin, fluvastatin, atorvastatin, itavastatin, rosuvastatin and rivastatin.

Yet even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is simvastatin, atorvastatin or rosuvastatin.

Another aspect of the invention that is of interest relates to a method for delaying the onset or reducing the risk of developing atherosclerosis in a human patient in need of such treatment comprising administering to said patient effective amounts of a compound of formula as described above and a cholesterol absorption inhibitor. More particularly, another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor wherein the cholesterol absorption inhibitor is ezetimibe.

Another aspect of the invention that is of interest relates to a method for delaying the onset or reducing the risk of developing the other diseases and conditions mentioned above, in a mammalian patient in need of such treatment comprising administering to said patient effective amounts of a compound of formula I as described above, and a cholesterol absorption inhibitor.

More particularly, another aspect of the invention that is of interest relates to a method for delaying the onset or reducing the risk of developing the other diseases and conditions mentioned above, in a human patient in need of such treatment comprising administering to said patient effective amounts of a compound of formula I as described above, and a cholesterol absorption inhibitor, wherein the cholesterol absorption inhibitor is ezetimibe.

Another aspect of the invention that is of interest relates to a method of treating, delaying the onset, or preventing a condition selected from the group consisting of: hypercholesterolemia, atherosclerosis, low HDL levels, high LDL levels, hyperlipidermia, hypertriglyceridemia and dyslipidemia, in a mammalian patient in need of such treatment, comprising administering to the patient therapeutically effective amounts of a compound of formula I or a pharmaceutically acceptable salt or solvate thereof, and a CETP inhibiting compound.

More particularly, an aspect of the invention that is of interest relates to a method of treating, delaying the onset, or preventing a condition selected from the group consisting of: hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I or a pharmaceutically acceptable salt or solvate thereof, and a CETP inhibiting compound selected from torcetrapib and anacetrapib.

Another aspect of the invention that is of interest relates to a pharmaceutical composition comprising (1) a compound of formula I as described above; (2) a compound selected from the list provide above in combination with a pharmaceutically acceptable carrier.

One pharmaceutical composition that is of interest is comprised of a compound of formula I as described herein, or a pharmaceutically acceptable salt or solvate thereof, in combination with a DPP-IV inhibitor selected from the group consisting of:

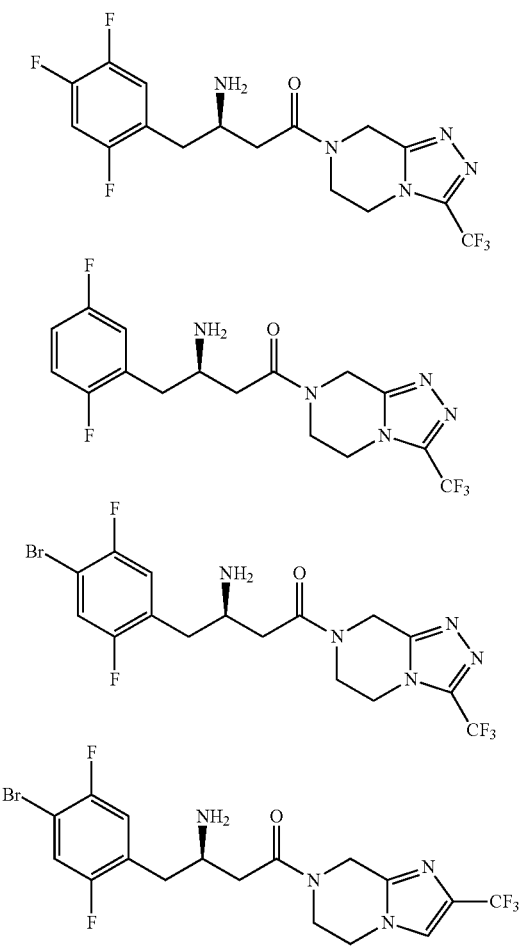

or a pharmaceutically acceptable salt or solvate thereof in combination with a pharmaceutically acceptable carrier.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed with the compounds of Formula I.

Salts and Solvates

Salts and solvates of compounds of formula I are included in the present invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I are intended to include the pharmaceutically acceptable salts and solvates.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within the formulas described herein can be prepared without undue experimentation by conventional techniques well known to those skilled in the art or by processes analogous to those described in the Schemes and Examples herein using appropriate isotopically-enriched reagents and/or intermediates.

This invention relates to a method of inhibiting the activity of glucagon by antagonizing the glucagon receptor, thereby reducing the rate of gluconeogenesis and glycogenolysis, and the concentration of glucose in plasma.

The compounds of formula I can be used in the manufacture of a medicament for the prophylactic or therapeutic treatment of disease states in mammals associated with elevated levels of glucose, comprised of combining the compound of formula I with the carrier materials to provide the medicament.

Dose Ranges

The prophylactic or therapeutic dose of a compound of formula I will, of course, vary with the nature or severity of the condition to be treated, the particular compound selected and its route of administration. It will also vary according to the age, weight and response of the individual patient. In general, the daily dose range lies within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds of formula I, as well as the pharmaceutically acceptable salts and solvates thereof, for adults range from about 0.1 mg to about 1.0 g per day, preferably about 1 mg to about 500 mg, in single or divided doses. Examples of suitable dosages include 0.1 mg, 1 mg, 2 mg, 5 mg, 10 mg, 20 mg, 40 mg, 50 mg, 75 mg, 100 mg, 150 mg, 200 mg, 250 mg, 500 mg, 1000 mg and similar such doses. Representative dosages of compounds used in combination with the compounds of formula I are known, or the determination thereof is within the level of skill in the art, taking into account the description provided herein.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of formula I per kg of body weight per day.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human, with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet may contain, for example, from about 0.1 mg to about 1.0 g of the active ingredient and each cachet or capsule contains from about 0.1 mg to about 500 mg of the active ingredient.

The following are examples of pharmaceutical dosage forms containing a compound of Formula I:

| Injectable Suspension (im.) | mg/mL | Tablet | Mg/tablet |
|---|---|---|---|
| Compound of Formula 1 | 10.0 | Compound of Formula 1 | 25.0 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 4.0 |
| Benzalkonium chloride | 1.0 | Magnesium Stearate | 2.5 |
| Water for injection | t.d. 1.0 mL | Total (approx.) | 460 mg |

| Capsule | mg/capsule | Aerosol | Per Canister |
|---|---|---|---|
| Compound of Formula 1 | 25.0 | Compound of Formula 1 | 250 mg |
| Lactose | 735 | Lecithin, NF Liq. Conc. | 1.2 mg |
| Mg Stearate | 1.5 | Trichloromethane, NF | 4.025 g |
| Total (approx.) | 761.5 mg | Dichlorodifluoromethane, NF | 12.15 g |

Combination Therapy

As previously described, the compounds of Formula I may be used in combination with other drugs that are used in the treatment/prevention/delaying the onset of type 2 diabetes mellitus, as well as other diseases and conditions described herein, for which compounds of Formula I are useful. Other drugs may be administered, by a route and in an amount commonly used, contemporaneously or sequentially with a compound of Formula I. When a compound of Formula I is used contemporaneously with one or more other drugs, a combination pharmaceutical composition containing such other drugs in addition to the compound of Formula I is preferred. Accordingly, the pharmaceutical compositions of the present invention include those that alternatively contain one or more other active ingredients, in addition to a compound of Formula I. Examples of other active ingredients that may be combined with a compound of Formula I, either administered separately or in the same pharmaceutical compositions, include, but are not limited to: (a) biguanides (e g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DPP-IV inhibitors, such as sitagliptin, vildagliptin, saxagliptin, and the like, such as those disclosed in U.S. Pat. No. 6,699,871B1 granted on Mar. 2, 2004 (g) LXR modulators and (h) secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide), and CB1 inhibitors, such as rimonabant and those compounds disclosed in WO 03/077847A2 published on Sep. 25, 2003 and in WO05/000809 A1 published on Jan. 6, 2005.

An aspect of the invention that is particular interest relates to a pharmaceutical composition that is comprised of a compound of formula I, or a pharmaceutically acceptable salt thereof, and a member selected from the group consisting of simvastatin, mevastatin, ezetimibe, atorvastatin, metformin, sibutramine, orlistat, Qnexa, topiramate, naltrexone, bupriopion, phentermine, losartan, hydrochlorothiazide, buformin, phenformin, troglitazone, pioglitazone, rosiglitazone, insulin, somatostatin, voglibose, miglitol, acarbose, sitagliptin, vildagliptin, saxagliptin, alogliptin, acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide, rimonabant and taranabant, in combination with a pharmaceutically acceptable carrier.

The weight ratio of the compound of the Formula I to the second active ingredient may be varied within wide limits and depends upon the effective dose of each active ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

When used in combination with other agents, the dosages noted above for the glucagon antagonist are provided along with the usual dose for the other medication. For example, when a DPP-IV inhibitor such as those disclosed in U.S. Pat. No. 6,699,871B1, is included, the DPP-IV inhibitor can be used in an amount ranging from about 1.0 mg to as high as about 1000 mg, preferably about 2.5 mg to about 250 mg, and in particular, about 50 mg or about 100 mg administered in single daily doses or in divided doses as appropriate. Similarly, when the glucagon receptor antagonist is used in combination with a CB1 antagonist/inverse agonist, the CB1 antagonist/inverse agonist can be used in an amount ranging from as low as about 0.1 mg to as high as about 1000 mg, more particularly, in an amount ranging from about 1.0 mg to about 100 mg, and even more particularly, in an amount from about 1.0 mg to about 10 mg, administered in single daily doses or in divided doses as appropriate. Examples of doses of CB1 antagonist/inverse agonist include 1 mg, 2 mg, 3 mg, 4 mg, 5 mg, 6 mg, 7 mg, 8 mg, 9 mg, 10 mg and 20 mg.

Methods of Synthesis:

Compounds of the present invention can be prepared according to the Schemes provided below as well as the procedures provided in the Examples. The substituents are the same as in the above Formulas except where defined otherwise or otherwise apparent to the ordinary skilled artisan.

The novel compounds of the present invention can be readily synthesized using techniques known to those skilled in the art, such as those described, for example, in *Advanced Organic Chemistry*, March, 5$^{th}$ Ed., John Wiley and Sons, New York, N.Y., 2001; *Advanced Organic Chemistry*, Carey and Sundberg, Vol. A and B, 3$^{rd}$ Ed., Plenum Press, Inc., New York, N.Y., 1990; *Protective groups in Organic Synthesis*, Green and Wuts, 2$^{nd}$ Ed., John Wiley and Sons, New York, N.Y., 1991; *Comprehensive Organic Transformations*, Larock, VCH Publishers, Inc., New York, N.Y., 1988; *Handbook of Heterocyclic Chemistry*, Katritzky and Pozharskii, 2$^{nd}$ Ed., Pergamon, New York, N.Y., 2000 and references cited therein. The starting materials for the present compounds may be prepared using standard synthetic transformations of chemical precursors that are readily available from commercial sources, including Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Acros, (Pittsburgh, Pa.); BioBlocks, Inc. (San Diego, Calif.); and Trans World Chemicals (Rockville, Md.).

The procedures described herein for synthesizing the compounds may include one or more steps of protecting group manipulations and of purification, such as, re-crystallization, distillation, column chromatography, flash chromatography, thin-layer chromatography (TLC), and high-pressure chromatography (HPLC). The products can be characterized using various techniques well known in the chemical arts, including proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g, toluene, xylenes), halogenated solvents (e.g, methylene chloride, chloroform, carbontetrachloride, chlorobenzenes), ethers (e.g. diethyl ether, diisopropylether, tert-butyl methyl ether, diglyme, tetrahydrofuran, dioxane, anisole), nitriles (e.g, acetonitrile, propionitrile), ketones (e.g, 2-butanone, dithyl ketone, tert-butyl methyl ketone), alcohols (e.g, methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyllithium, phenyllithium, alkyl magnaesium halides, organic bases such as trimethylamine, triethylamine, triisopropylamine, N,N-diisopropylethyl amine, piperidine, N-methyl piperidine, morpholine, N-methyl morpholine, pyridine, collidines, lutidines, and 4-dimethylaminopyridine; and bicyclic amines such as DBU and DABCO.

It is understood that the functional groups present in compounds described in the Schemes below can be further manipulated, when appropriate, using the standard functional group transformation techniques available to those skilled in the art, to provide desired compounds described in this invention.

Throughout the synthesis schemes, abbreviations are used with the following meanings unless otherwise indicated:

| | |
|---|---|
| AIBN = azobisisobutyronitrile | act = aqueous |
| BINAP = 2,2'-bis(diphenylphosphino)-1,1'-binaphthalene | Bn = benzyl |
| BOC, Boc = t-butyloxycarbonyl | BOP = benzotriazol-1-yloxy-tris(dimethylamino)-phosphonium hexafluorophosphate |
| Bu = butyl, t-Bu = t-butyl | BuLi, n-BuLi = n-butyllithium |
| CBZ, Cbz = Benzyloxycarbonyl | CDI = 1,1'-carbonyldiimidazole |
| (S)-DAIPEN = (S)-1,1-di(4-anisyl)-2-isopropyl-1,2-ethylenediamine = (S)-1,1-bis(4-methoxyphenyl)-3-methylbutane-1,2-diamine | dba = dibenzylideneacetone = trans,trans-1,5-diphenyl-1,4-pentadien-3-one |
| DCM = dichloromethane | 2,4-diClPh = 2,4-dichlorophenyl |
| DIPEA = DIEA = diisopylethylamine | DMAP = 4-Dimethylaminopyridine |
| DMF = N,N-dimethylformamide | DMS = dimethyl sulfide |
| DMSO = dimethyl sulfoxide | dppf = 1,1'-bis(diphenylphosphino)ferrocene |
| EDC = 1-ethyl-3-(3-dimethylaminopropyl)-carbodiimide | eq. = equivalent(s) |
| Et = ethyl | EtOAc = ethyl acetate |
| EtOH = ethanol | g = gram(s) |
| HATU = O-(7-azabenzotriazol-1-yl)-N,N,N',N'-tetramethyluronium hexafluorophosphate | HOBT, HOBt = 1-hydroxybenzotriazole |
| HPLC = High pressure liquid chromatography | IPA = isopropanol = 2-propanol |
| iPr = isopropyl = 2-propyl | KHMDS = potassium bis(trimethylsilyl)amide |
| KOtBu = potassium tert-butoxide | LC/MS = liquid chromatography-mass spectrometry |
| LDA = lithium diisopropylamide | LHMDS = lithium bis(trimethylsily)amide |
| M = molar | mCPBA = 3-chloroperoxybenzoic acid |
| Me = methyl | MeCN, CH$_3$CN = acetonitrile |
| MeOH = methanol | mg = milligram(s) |
| mL = milliliter(s) | mmol = millimole(s) |
| MTBE = TBME = methyl t-butyl ether | N = normal |
| NaOtBu = sodium tert-butoxide | NBS = N-bromosuccinimide |
| NCS = N-chlorosuccinimide | NMP = 1-methyl-2-pyrrolidinone |
| n-Pr = n-propyl | PCC = pyridinium chlorochromate |
| Pd/C = palladium on activated carbon | Ph = phenyl |
| PyBOP = Benzotriazol-1-yloxytripyrrolidinophosphonium hexafluorophosphate | RT, rt = room temperature |
| TBAF = tetrabutylammonium fluoride | Tf = triflate = trifluoromethanesulfonate |
| TFA = Trifluoroacetic acid | THF = tetrahydrofuran |
| TMS = trimethylsilyl | Tr = trityl = triphenylmethyl |

(S)-xyl-SEGPHOS =
(S)-5,5'-Bis[di(3,5-xylyl)phosphino]-4,4'-bi-1,3-benzodioxole

Compounds of the present invention may be prepared according to the methodology outlined in the following general synthetic schemes.

Multiple embodiments of the present invention are summarized in Scheme 1 which depicts the preparation of compounds Ia, Ib, and Ic from the carboxylic acid 1. The carboxylic acid intermediate 1 is coupled with substituted or unsubstituted beta alanine ester (either methyl or ethyl ester) or glycine ester (either methyl or ethyl ester) using O-(7-azabenzotriazol-1-yl)-N,N,N',N'-tetramethyluronium hexafluorophosphate (HATU) and a base, generally N,N-diisopropylethylamine (DIEA), in a solvent such as N,N-dimethylformamide (DMF), 1-methyl-2-pyrrolidinone (NMP), or dichloromethane (DCM) at ambient temperature to yield compound 2. Alternatively, the conversion of 1 to 2 may be carried out with EDC, HOBt, and a base such as DIEA in similar solvents as those used with HATU and DIEA. Many additional peptide coupling conditions are known and may also be used. Saponification of ester 2 to give compound Ia is achieved with a base such as aqueous lithium hydroxide (LiOH) or aqueous sodium hydroxide in a polar solvent such as tetrahydrofuran, methanol, ethanol or a mixture of similar solvents. In additional embodiments of the invention, compounds Ib and Ic may be prepared directly from acid 1 by coupling with the appropriately substituted amine using the peptide coupling methods described for the preparation of amide 2.

Scheme 1

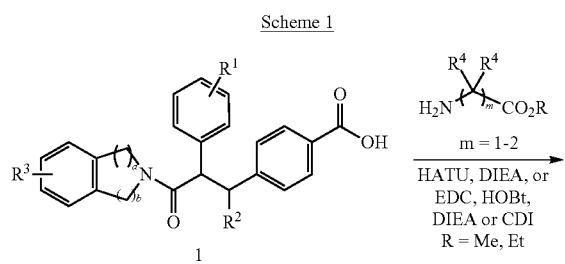

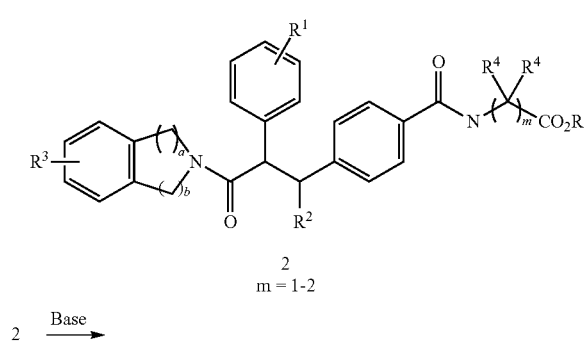

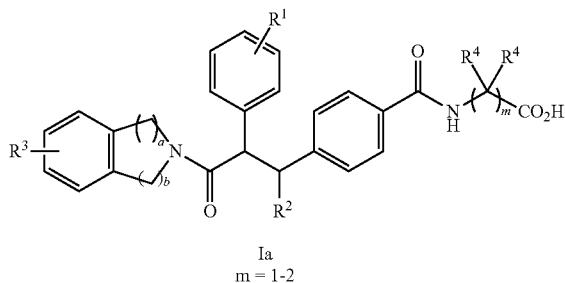

Ia
m = 1-2

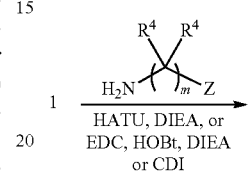

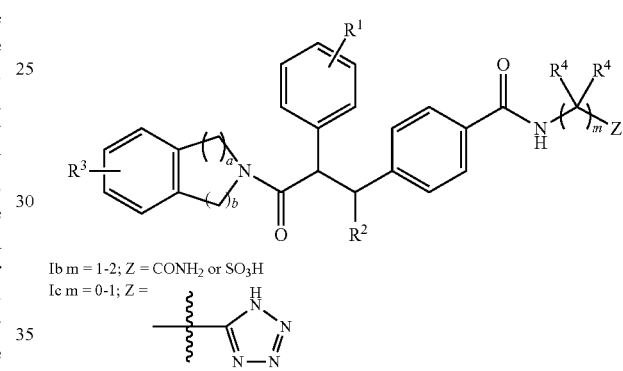

Ib m = 1-2; Z = CONH$_2$ or SO$_3$H
Ic m = 0-1; Z =

Carboxylic acid intermediate 1 may be prepared from diester 3 as shown in Scheme 2. The t-butyl ester of 3 may be selectively deprotected to afford acid 4 using an acid such as acetic acid or trifluoroacetic acid (TFA). Condensation of acid 4 with an appropriate amine 5 to afford amide 6 may be accomplished using the various peptide coupling conditions described for the conversion of 1 to 2 (Scheme 1). Amines 5 may be commercially available or may be readily prepared by one skilled in the art of organic synthesis using various procedures described in the chemical literature. Carboxylic acid 1 may be accessed from amide 6 by saponifying the methyl ester using the conditions described for the conversion of 2 to Ia (Scheme 1).

Scheme 2

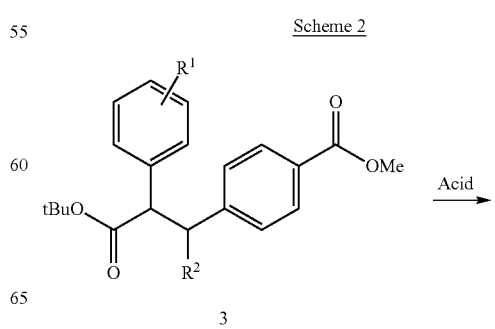

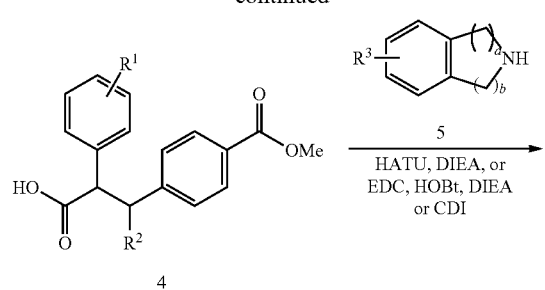

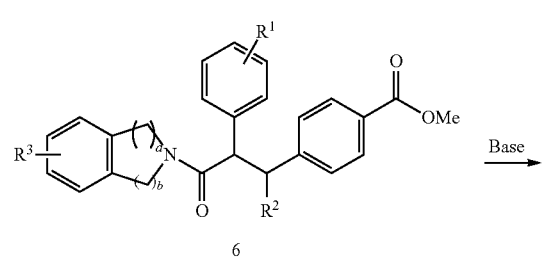

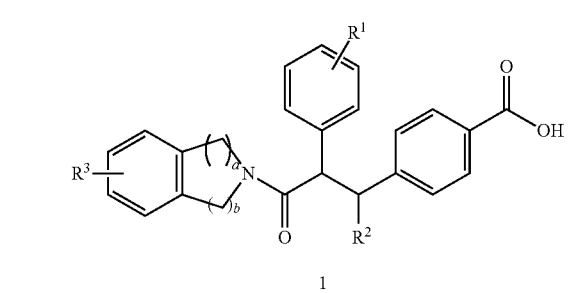

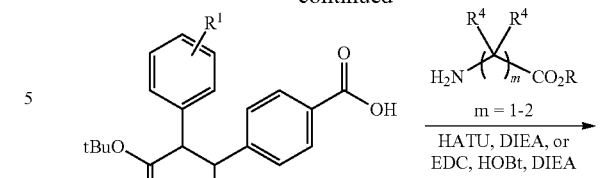

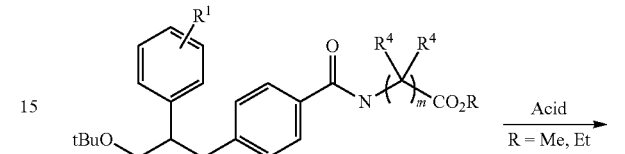

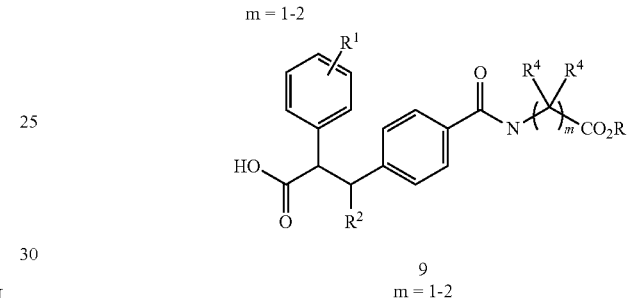

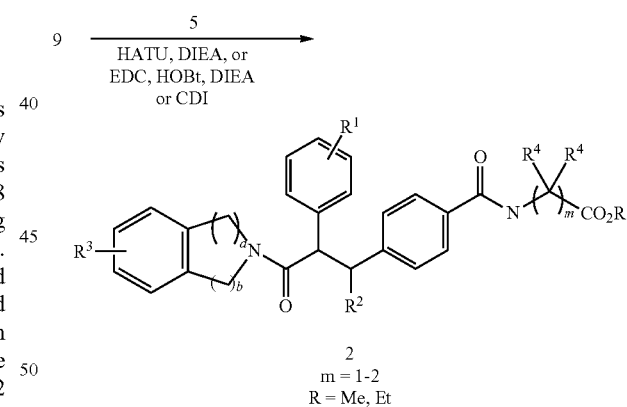

Diester 3 may also be converted to amide intermediate 2 as shown in Scheme 3. The methyl ester of 3 may be selectively deprotected to afford acid 7 using basic conditions as described for the conversion of 2 to Ia (Scheme 1). Amide 8 can then be prepared from acid 7 using the peptide coupling conditions described for the conversion of 1 to 2 (Scheme 1). Selective deprotection of the t-butyl ester of amide 8 to afford acid 9 can be conducted under acidic conditions as described for the conversion of 3 to 4 (Scheme 2). Finally, amine 5 can be condensed with acid 9 to afford amide 2 using the peptide coupling conditions described for the conversion of 1 to 2 (Scheme 1).

Scheme 3

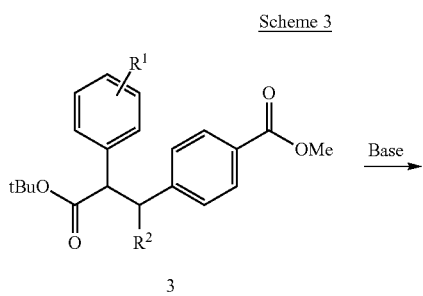

While the $R^3$ substituents are typically present in the starting amines 5 (Schemes 2 and 3), it is also possible to alter the $R^3$ substituents on advanced intermediates as shown in Scheme 4. For instance, the bromo substituent of intermediate 2a (which can be prepared according to Scheme 3) can be functionalized under Suzuki coupling conditions with an aryl or heteroaryl boronic acid 10, palladium catalyst such as $(PPh_3)_2PdCl_2$, base such as sodium carbonate, in a mixed solvent system such as acetonitrile and water, at temperatures between 70° C. and 200° C. Under these conditions, the ethyl ester of intermediate 2a can also be hydrolyzed to afford compound Ia directly. Numerous other metal-mediated functionalizations of intermediates such as 2a will be obvious to those skilled in the art.

Scheme 4

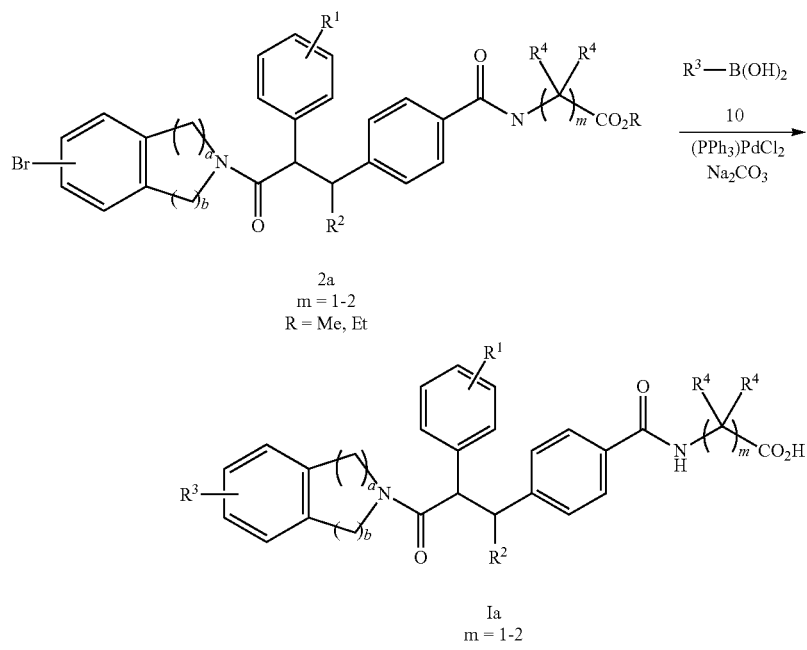

$R^3$ = Aryl or Heteroaryl

The preparation of diester 3 is summarized in Scheme 5. Commercially available aldehyde 11 can be converted to alcohol 12 by nucleophilic addition of an organometallic reagent such as an alkyllithium or alkylmagnesium in an ether solvent such as THF at temperatures between −78° C. and room temperature. Bromide 13 can be accessed by treating alcohol 12 with brominating reagents such as $CBr_4$ and $PPh_3$ in a solvent such as DCM. Alkylation of ester 14 with benzyl bromide 13 can be mediated by bases such as LHMDS or KOtBu in polar aprotic solvents such as DMF or DMSO to provide a mixture of diastereomers of diester 3. A wide variety of esters 14 may be commercially available, or are readily prepared using methods familiar to those skilled in the art.

Scheme 5

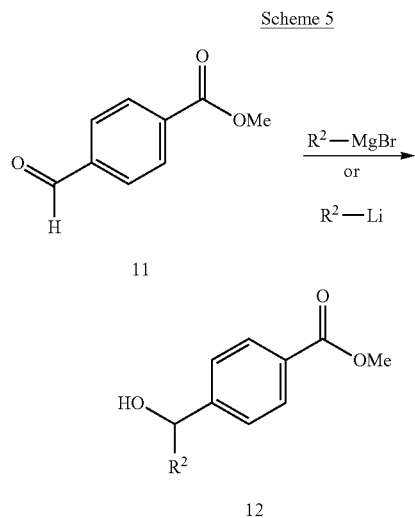

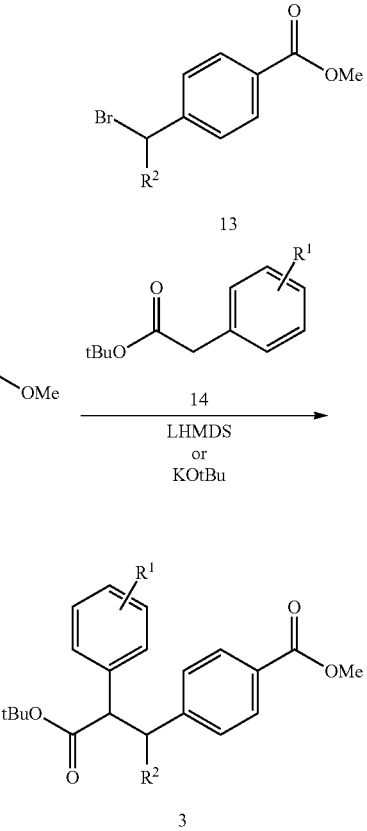

Separation of diastereomers can be carried out at various stages in the preparation of the desired final amides; however, it is typically carried out on intermediate 8 using silica gel chromatography. Separation of enantiomeric pairs is achieved by normal-phase HPLC or supercritical fluid chromatography using a chiral column available from Daicel®. Resolution of enantiomers is also typically carried out on intermediate 8.

Analytical HPLC mass spectrometry conditions:

LC1:
  Column: Waters Xterra MS C-18, 3.5 μm, 3.0×50 mm
  Temperature: 50° C.
  Eluent 10:90 to 98:2 v/v acetonitrile/water+0.05% TFA over 3.75 min.
  Flow Rate: 1.0 mL/min, Injection 10 μL
  Detection: PDA, 200-600 nm
  MS: mass range 150-750 amu; positive ion electrospray ionization LC2:
  Column: Waters Xterra IS C-18, 3.5 μm, 2.1×20 mm
  Temperature: 50° C.
  Eluent: 5:95 to 95:5 v/v acetonitrile/water+0.05% TFA over 1.75 min.
  Flow Rate: 1.5 mL/min, Injection 5 μL
  Detection: PDA, 200-600 nm
  MS: mass range 150-750 amu; positive ion electrospray ionization LC3:
  Column: Waters Xterra IS C-18, 3.5 μm, 2.1×20 mm
  Temperature: 50° C.
  Eluent 5:95 to 95:5 v/v acetonitrile/water+0.05% TFA over 3.00 min.
  Flow Rate: 1.5 mL/min, Injection 5 μL
  Detection: PDA, 200-600 nm
  MS: mass range 150-750 amu; positive ion electrospray ionization LC4:
  Column: Waters Xterra IS C-18, 3.5 μm, 3.0×50 mm
  Temperature: 50° C.
  Eluent: 10:90 to 98:2 v/v acetonitrile/water+0.05% TFA over 1.25 min.
  Flow Rate: 1.5 mL/min, Injection 5 μL
  Detection: PDA, 200-600 nm
  MS: mass range 150-750 amu; positive ion electrospray ionization LC5:
  Column: Sunfire C-18, 5 μm, 4.6×100 mm
  Temperature: 50° C.
  Eluent: 10:90 to 98:2 v/v acetonitrile/water+0.1% formic acid over 1.25 min.
  Flow Rate: 1.5 mL/min, Injection 5 μL
  Detection: PDA, 200-600 nm
  MS: mass range 150-750 amu; positive and negative ion electrospray ionization LC6:
  Column: Agilent ZOBAX SB-C18, 3.5 μm, 2.1×50 mm
  Temperature: 50° C.
  Eluent: 10:90 to 100:0 v/v acetonitrile/water+0.05% TFA over 4.00 min.
  Flow Rate: 0.8 mL/min, Injection 1 μL
  Detection: PDA, 200-400 nm
  MS: mass range 100-1000 amu; positive ion electrospray ionization Preparative reverse phase HPLC (RP-HPLC) conditions:
  Column: Xterra MS, 5 μM, 30×100 mm
  Flow Rate: 40.0 mL/min
  Eluent: acetonitrile/water+0.1% TFA
  Gradient: 10 to 100 v/v acetonitrile/water+0.1% TFA over 20.0 min.
  Temperature: ambient
  Detection: PDA, 254 nm Preparative thin layer chromatography (PTLC) was performed on 20×20 cm plates (500 μm thick silica gel) using hexanes/ethyl acetate or (DCM/MTBE)/hexanes or DCM/hexanes as eluent. Silica gel chromatography was conducted on a Biotage Horizon flash chromatography system using a hexanes/ethyl acetate, (DCM/MTBE)/hexanes or DCM/hexanes gradient.

The following examples are provided so that the invention might be more fully understood. They should not be construed as limiting the invention in any way.

INTERMEIDATE 1

Methyl 4-{1-[2-tert-butoxy-1-(4-chlorophenyl)-2-oxoethyl]butyl}benzoate

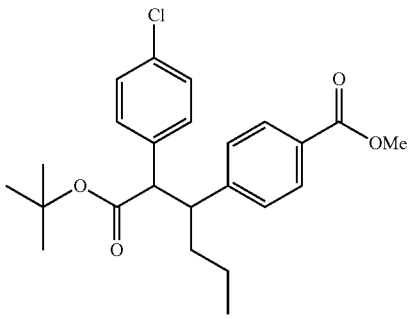

Step A. Methyl 4-(1-hydroxybutyl)benzoate

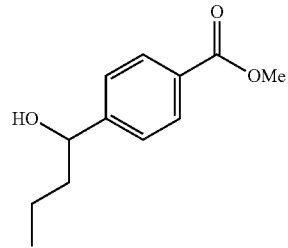

Propylbromide (13.4 g, 11.0 mmol) was added dropwise to a slurry of magnesium dust (2.64 g, 11.0 mmol) in THF (100 mL) at 40-45° C. After being stirred for another 30 minutes, the solution was cooled to room temperature then added dropwise to a solution of methyl 4-formylbenzoate (16.4 g, 10.0 mmol) in THF (120 mL) at −40° C. Once the addition was complete, the mixture was allowed to warm to room temperature and was stirred overnight before being diluted with saturated $NH_4Cl$ (aq) then EtOAc. The organic layer was washed with water then brine, dried over anhydrous $Na_2SO_4$, filtered, then concentrated. The residue was purified by silica gel chromatography eluting with 5% EtOAc/petroleum ether to afford the title compound. $^1$H NMR (300 MHz, $CDCl_3$) δ 7.96 (d, J=6 Hz, 2 H); 7.37 (d, J=6 Hz, 2 H); 4.70 (t, J=7 Hz, 1 H); 3.87 (s, 3 H); 2.40 (s, 1 H); 1.65-1.76 (m, 2 H); 1.27-1.47 (m, 1 H); 0.90 (t, J=7.2 Hz, 3 H).

Step B. Methyl 4-(1-bromobutyl)benzoate

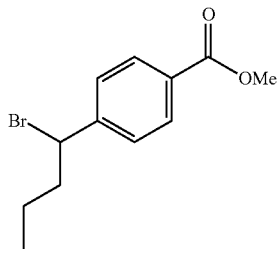

A solution of PPh₃ (42.2 g. 320 mmol) in DCM (200 mL) was added dropwise to a solution of methyl 4-(1-hydroxybutyl)benzoate (33.5 g, 160 mmol) and CBr₄ (53.1 g, 320 mmol) in DCM (1200 mL) at 0° C. Once the addition was complete, the mixture was allowed to warm to room temperature and was stirred overnight. The mixture was concentrated, then the resulting residue was purified by silica gel chromatography eluting with 5% EtOAc/petroleum ether to afford the title compound. ¹H NMR (300 MHz, CDCl₃) δ 8.00 (d, J=6 Hz, 2 H); 7.45 (d, J=6 Hz, 2 H); 4.95 (t, J=7 Hz, 1 H); 3.91 (s, 3 H); 2.19-2.32 (m, 1 H); 2.02-2.14 (m, 1 H); 1.43-1.55 (m, 1 H); 1.24-1.38 (m, 1 H); 0.93 (t, J=7 Hz, 3 H).

Step C. Methyl 4-{1-[2-tert-butoxy-1-(4-chlorophenyl)-2-oxoethyl]butyl}benzoate

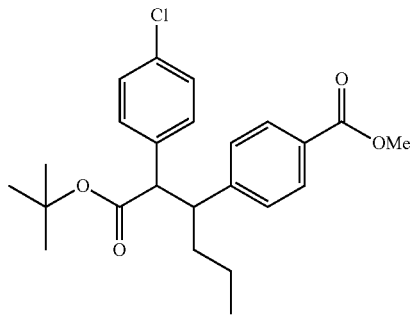

To a suspension of KOtBu (980 mg, 8.73 mmol) in anhydrous DMF (15 mL) at 0° C. was added tert-butyl 4-chlorophenylacetate (1.80 g, 7.94 mmol). After stirring for two minutes, a solution of methyl 4-(1-bromobutyl)benzoate in DMF (5 mL) was added dropwise. The mixture was allowed to warm to room temperature. After stirring for 20 minutes, water was added then the solution was extracted with CH₂Cl₂ (2×100 mL). The combined organic layers were washed with saturated NH₄Cl (aq) (20 mL) then saturated NaCl (aq) (20 mL), dried over Na₂SO₄, filtered, then concentrated. The residue was purified by silica gel chromatography eluting with 2% EtOAc/petroleum ether to afford the title compound. ¹H NMR (300 MHz, CD₃OD) δ 7.98-8.02 (m, 2 H), 7.77-7.81 (m, 2 H), 7.38-7.44 (m, 2 H), 7.09-7.13 (m, 2 H), 3.91 (s, 3 H), 3.79-3.81 (m, 1 H), 3.34-3.40 (m, 1 H), 1.20-1.30 (m, 2 H), 1.03 (s, 9 H), 0.91-1.02 (m, 2 H), 0.68 (t, J=7.4 Hz, 3 H).

EXAMPLE 1

N-[4-(1-{1-(4-chlorophenyl)-2-oxo-2-[4-(trifluoromethyl)-1,3-dihydro-2H-isoindol-2-yl]ethyl}butyl)benzoyl]-β-alanine

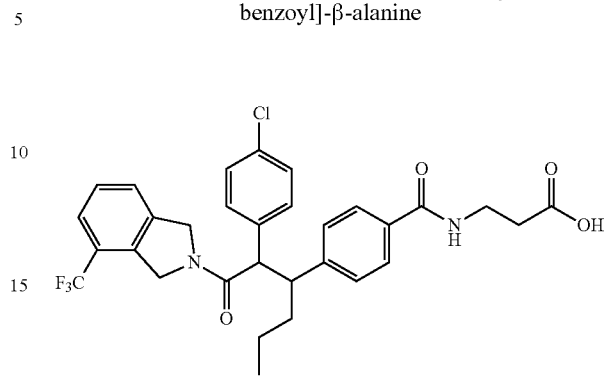

Step A. 4-{1-[2-tert-butoxy-1-(4-chlorophenyl)-2-oxoethyl]butyl}benzoic acid

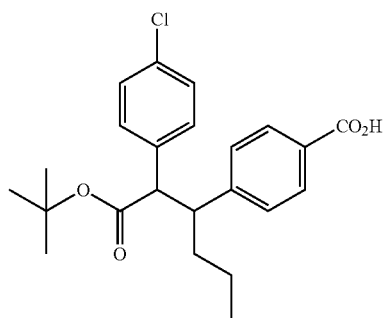

To a solution of INTERMEDIATE 1 (20 g, 48 mmol) in MeOH was slowly added 5N NaOH (5N in H₂O, 19 mL, 95 mmol) at ambient temperature. Once all INTERMEDIATE 1 was consumed by LC-MS analysis, the mixture was concentrated. The residue was partitioned between EtOAc and 1N HCl (aq). The organic layer was then washed with water then saturated NaCl (aq). The organic layer was then dried over Na₂SO₄, filtered, then concentrated. The resulting acid was used directly for the following step. ¹H NMR (400 MHz, DMSO-d₆) δ 12.80 (s, 1 H); 7.89 (s, 1 H); 7.87 (s, 1 H); 7.48-7.65 (m, 2 H); 7.45-7.74 (m, 3 H); 7.15 (s, 1 H); 3.87 (d, J=11.6 Hz, 1 H); 3.15-3.11 (m, 1 H); 1.61-1.70 (m, 1 H); 1.06-1.14 (m, 1 H); 0.97 (s, 9 H); 0.76-0.86 (m, 2 H); 0.56 (t, J=7.6 Hz, 3 H). LC1 2.54 min. (M−tBu+H)⁺ 347.

Step B. tert-Butyl 2-(4-chlorophenyl)-3-(4-{[(3-ethoxy-3-oxopropyl)amino]carbonyl}phenyl)hexanoate

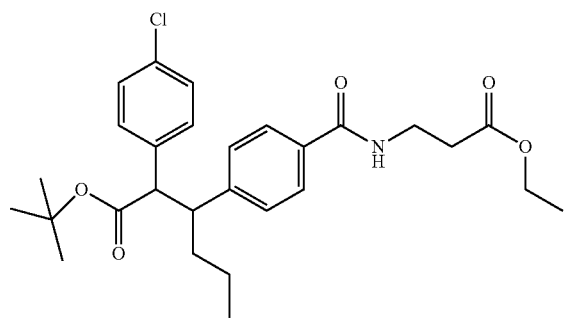

To a solution of 4-{1-[2-tert-butoxy-1-(4-chlorophenyl)-2-oxoethyl]butyl}benzoic acid (17.8 g, 44 mmol) in DCM (175 mL) at room temperature was added β-alanine ethyl ester hydrochloride (6.6 g, 44 mmol), HOBt (7.85 g, 52.8 mmol), EDC (9.8 g, 53 mmol) and Et₃N (30 mL, 220 mmol). After being stirred for 16 hours, the mixture was diluted with DCM then washed with water then saturated NaCl (aq). The organic layer was dried over Na₂SO₄, filtered, then concentrated. The resulting residue was purified by silica gel chromatography eluting with 0-100% EtOAc/hexanes. The two diastereomeric title compounds were separated by silica gel chromatography eluting with 40% EtOAc/hexanes. The slower-eluting diastereomer is readily resolved to provide enantiopure material by supercritical fluid chromatography on a ChiralPak IA column (3 cm×25 cm) eluting with 50 mL/min of 10% (2:1:3 MeOH:CH₃CN:CHCl₃) and 90% CO₂ at 35° C. and 100 bar.

Faster-eluting diastereomer: ¹H NMR (500 MHz, CDCl₃): δ 7.54 (d, J=7.2 Hz, 2 H); 7.31-7.29 (m, 1 H); 7.07-7.03 (m, 5 H); 6.76 (br, 1 H); 4.21-4.13 (m, 2 H); 3.72-3.68 (m, 2 H); 3.64-3.62 (d, J=11.2 Hz, 1 H); 3.34-3.29 (m, 1 H); 2.64-2.62 (m, 2 H); 1.82-1.68 (m, 2 H); 1.46 (s, 9 H); 1.30-1.27 (t, J=5.3 Hz, 3 H); 1.14-1.09 (m, 2 H); 0.97-0.85 (t, J=7.1 Hz, 3 H).

Slower-eluting diastereomer: ¹H NMR (500 MHz, CDCl₃): δ 7.68-7.52 (d, J=6.2 Hz, 2 H); 7.43-7.42 (d, J=6.2 Hz, 2 H); 7.38-7.36 (m, 4 H); 6.88 (s, 1 H); 4.23-4.19 (m, 2 H); 3.77-3.75 (m, 2 H); 3.69-3.66 (d, J=11.4 Hz, 1 H); 3.25-3.21 (t, J=10.9 Hz, 1 H); 2.69-2.67 (m, 2 H); 1.62 (br, 2 H); 1.33-1.29 (m, 3 H); 1.09 (s, 9 H); 0.97-0.94 (m, 2 H); 0.71-0.68 (t, J=5.0 Hz, 3 H).

Step C: 2-(4-Chlorophenyl)-3-(4-{[(3-ethoxy-3-oxopropyl)amino]carbonyl}phenyl)hexanoic acid

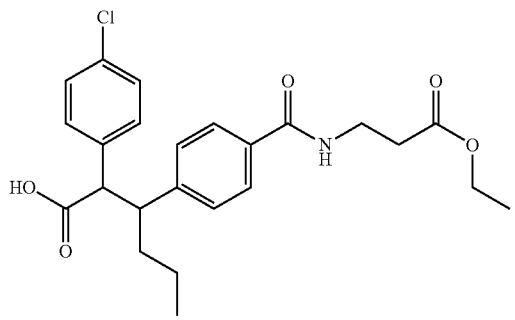

To a solution of the slower-eluting diastereomer of tert-butyl 2-(4-chlorophenyl)-3-(4-{[(3-ethoxy-3-oxopropyl)amino]carbonyl}phenyl)hexanoate (1.9 g, 3.8 mmol) in DCM (20 mL) at 0° C. was added TFA (20 mL) over 1 min. After being stirred for 30 minutes, the solution was concentrated to afford the title compound. After being dried on high vacuum overnight, the material was used directly for the next step. LC1 2.09 min. (M+H)⁺ 446.

Step D. N-[4-(1-{1-(4-Chlorophenyl)-2-oxo-2-[4-(trifluoromethyl)-1,3-dihydro-2H-isoindol-2-yl]ethyl}butyl)benzoyl]-β-alanine

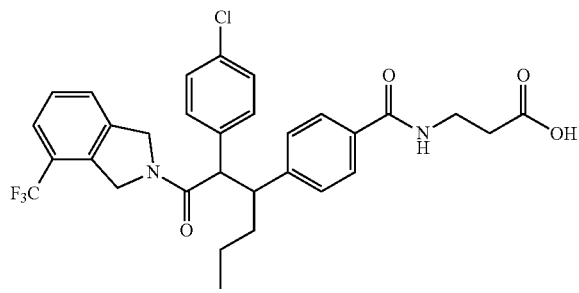

To a solution of (2-(4-chlorophenyl)-3-(4-{[(3-ethoxy-3-oxopropyl)amino]carbonyl}phenyl)hexanoic acid) (30 mg, 0.07 mmol) in NMP (1 mL) at room temperature was added HATU (29 mg, 0.08 mmol). After one hour, DIPEA (61 μL, 0.21 mmol) and 4-(trifluoromethyl)isoindoline hydrochloride (20 mg, 0.09 mmol) was added. After being stirred at room temperature overnight, the mixture was diluted with 1N HCl then extracted twice with EtOAc. The organic layers were combined, dried over Na₂SO₄, filtered, then concentrated. The resulting material was used directly for the next step. LC2 1.30 min. (M+H)⁺ 615.4.

The product from the previous step was dissolved in THF/MeOH/water (2 mL) then LiOH (1 N in H₂O, 0.2 mL, 0.2 mmol) was added. Once all starting material had been consumed by LC-MS analysis, the mixture was diluted with 1N HCl then extracted twice with EtOAc. The organic layers were combined, dried over Na₂SO₄, filtered, then concentrated. The resulting residue was purified by reverse-phase HPLC. Following lyophilization, this afforded the title compound as a white solid. The characterization data provided are for a single stereoisomer (of the possible four) that was the most potent glucagon receptor antagonist. ¹H NMR (600 MHz, CD₃OD): δ 7.71 (d, J=8.0 Hz, 2 H); 7.59 (dd, J=8.4, 6.5 Hz, 2 H); 7.54-7.45 (m, 4 H); 7.44-7.38 (m, 3 H); 4.98-4.78 (m, 2 H); 4.62-4.45 (m, 1 H); 4.46-4.31 (m, 1 H); 4.25 (dd, J=11.0, 7.3 Hz, 1 H); 3.58-3.53 (m, 2 H); 3.49-3.41 (m, 1 H); 2.60-2.55 (m, 2 H); 1.59-1.47 (m, 1 H); 1.29-1.19 (m, 1 H); 1.01-0.88 (m, 2 H); 0.69 (t, J=7.4 Hz, 3 H). LC2 1.27 min. (M+H)⁺ 587.4

EXAMPLE 2

N-(4-{1-[1-(4-chlorophenyl)-2-(3,4-dihydroquinolin-1(2H)-yl)-2-oxoethyl]butyl}benzoyl)-β-alanine

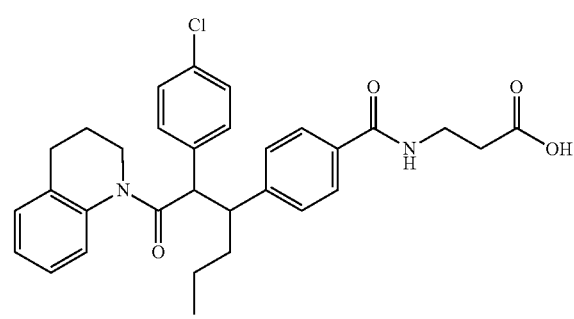

Using the procedure from EXAMPLE 1, 1,2,3,4-tetrahydroquinoline and INTERMEDIATE 1 were converted to the title compound. The characterization data provided are for a single stereoisomer (of the possible four) that was the most potent glucagon receptor antagonist. $^1$H NMR (CD$_3$OD, 400 MHz) δ 7.40-7.70 (m, 7 H); 7.02-7.35 (m, 5 H); 3.72-3.90 (m, 1 H); 3.62-3.70 (m, 1 H); 3.43-3.60 (m, 2 H); 3.30-3.40 (m, 2 H); 2.85-3.05 (m, 2 H); 2.40-2.55 (m, 2 H); 2.00-2.22 (m, 2 H); 1.20-1.40 (m, 2 H); 0.80-1.00 (m, 2 H); 0.68 (t, J=7.2 Hz, 3 H). LC2 1.44 min. (M+H)$^+$ 533.

EXAMPLE 3

N-(4-{1-[1-(4-chlorophenyl)-2-(2,3-dihydro-1H-indol-1-yl)-2-oxoethyl]butyl}benzoyl)-β-alanine

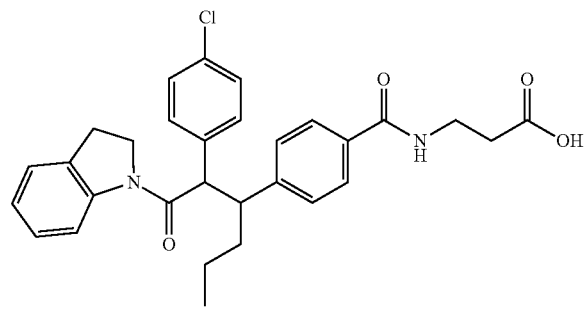

Using the procedure from EXAMPLE 1, indoline and INTERMEDIATE 1 were converted to the racemic title compound. The characterization data provided are for the diastereomer that was the more potent glucagon receptor antagonist. $^1$H NMR (CD$_3$OD, 300 MHz) δ 7.48-7.90 (m, 6 H); 7.12-7.25 (m, 3 H); 6.85-7.10 (m, 3 H); 4.22-4.55 (m, 1 H); 3.90-4.20 (m, 2 H); 3.40-3.68 (m, 4 H); 2.90-3.04 (m, 1 H); 2.55-2.68 (m, 2 H); 1.70-1.95 (m, 1 H); 1.45-1.65 (m, 1 H); 1.15-1.22 (m, 2 H); 0.70 (t, J=7.4 Hz, 3 H). MS (M+H)$^+$ 519.

EXAMPLE 4

N-[4-(1-{1-(4-chlorophenyl)-2-[5-(2-methoxypyridin-3-yl)-1,3-dihydro-2H-isoindol2-yl]-2-oxoethyl}butyl)benzoyl]-β-alanine

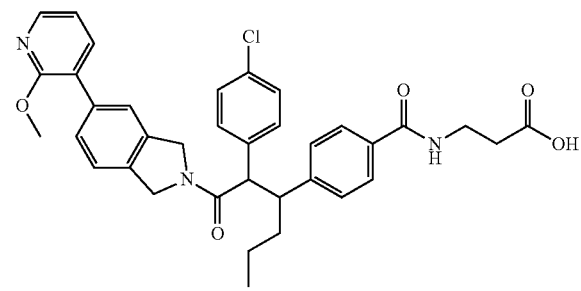

Step A. Ethyl N-(4-{1-[2-(5-bromo-1,3-dihydro-2H-isoindol-2-yl)-1-(4-chlorophenyl)-2-oxoethyl]butyl}benzoyl)-β-alaninate

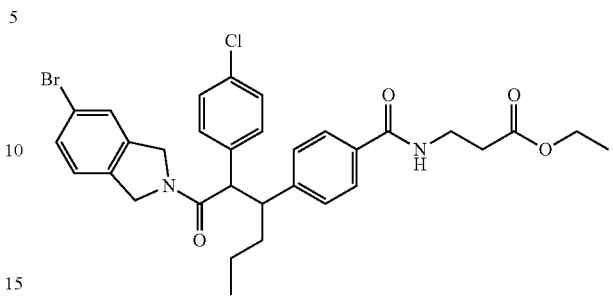

To a solution of a single stereoisomer (of the four possible) of 2-(4-chlorophenyl)-3-(4-{[(3-ethoxy-3-oxopropyl)amino]carbonyl}phenyl)hexanoic acid (EXAMPLE 1, Step C, 142 mg, 0.318 mmol) in NMP (3 mL) at room temperature was added HATU (133 mg, 0.350 mmol) and DIPEA (222 μl, 1.27 mmol). After one hour, 5-bromoisoindoline (94 mg, 0.48 mmol) was added, then the mixture was stirred at rt until the reaction was complete by LC-MS analysis. The mixture was then diluted with EtOAc then washed with water then saturated NaCl (aq). The organic layer was then dried over Na$_2$SO$_4$, filtered, then concentrated. The resulting residue was purified by silica gel chromatography eluting with 0-100% EtOAc/hexanes to provide the title compound as a white solid. LC2 1.53 min. (M+H)$^+$ 627.

Step B. N-[4-(1-{1-(4-Chlorophenyl)-2-[5-(2-methoxypyridin-3-yl)-1,3-dihydro-2H-isoindol-2-yl]-2-oxoethyl}butyl)benzoyl]-β-alanine

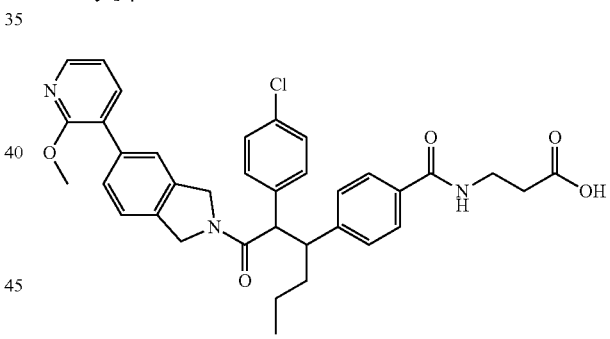

Ethyl N-(4-{1-[2-(5-bromo-1,3-dihydro-2H-isoindol-2-yl)-1-(4-chlorophenyl)-2-oxoethyl]butyl}benzoyl)-β-alaninate (30 mg, 0.048 mmol), trans-bis(triphenylphospine)palladium(II) chloride (3.4 mg, 4.8 μmol), 2-methoxypyridine-3-boronic acid (9.5 mg, 0.062 mmol), acetonitrile (2.0 mL) and Na$_2$CO$_3$ (2.0 M in H$_2$O, 2.0 mL, 4.0 mmol) were added to a microwave vial. DMF (0.3 mL) was added to increase the solubility of the bromide. The vial was flushed with nitrogen, sealed, then heated to 125° C. for 10 minutes in a microwave reactor. The mixture was diluted with 1N HCl (aq) then extracted twice with EtOAc. The organic layers were dried over Na$_2$SO$_4$, filtered, then concentrated. The resulting residue was purified by reverse-phase HPLC. Following lyophilization, this afforded the title compound as a white solid. The characterization data provided are for a single stereoisomer (of the possible four) that was the most potent glucagon receptor antagonist. $^1$H NMR (500 MHz, CD$_3$OD): δ 8.09 (ddd, J=13.2, 5.1, 1.8 Hz, 1 H); 7.72 (d, J=8.1 Hz, 2 H); 7.67-7.58 (m, 1 H); 7.61 (dd, J=8.6, 2.4 Hz, 2 H); 7.49 (d, J=8.0 Hz, 2 H); 7.43-7.35 (m, 2 H); 7.37 (d, J=8.0 Hz, 1 H); 7.32 (s, 1 H); 7.23 (dd, J=13.9, 8.0 Hz, 1 H); 7.01 (ddd, J=14.0, 7.3, 5.0 Hz, 1 H); 4.90 (obs, 1 H); 4.79 (d, J=14.5 Hz, 1 H); 4.47 (d, J=16.2 Hz, 1 H); 4.31 (d, J=16.2 Hz, 1 H); 4.26 (dd, J=11.1, 2.3 Hz, 1 H); 3.90 (d, J=15.6 Hz, 3 H); 3.56 (t, J=7.0 Hz, 2 H); 3.47 (dd, J=11.2, 3.4 Hz, 1 H); 2.58 (t, J=7.0 Hz, 2 H); 1.55-1.49 (m, 1 H); 1.30 - 1.23 (m, 1 H); 1.00-0.91 (m, 2 H); 0.69 (t, J=7.3 Hz, 3 H). LC2 1.43 min. (M+H)$^+$ 626.

EXAMPLE 5

N-[4-(1-{1-(4-chlorophenyl)-2-[5-(2-methoxypyridin-3-yl)-1,3-dihydro-2H-isoindol-2-yl]-2-oxoethyl}butyl)benzoyl]-β-alanine

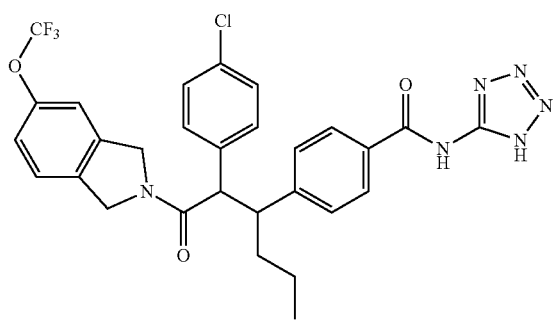

Step A. Methyl 4-(1-{1-(4-chlorophenyl)-2-oxo-2-[5-(trifluoromethoxy)-1,3-dihydro-2H-isoindol-2-yl]ethyl}butyl)benzoate

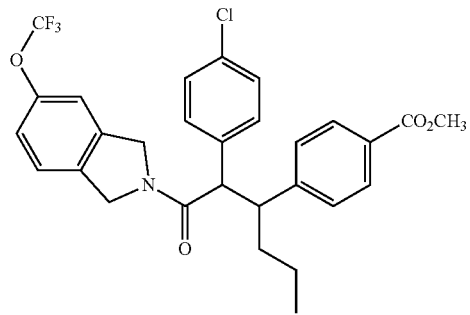

Trifluoroacetic acid (10 mL) was added to a solution of INTERMEDIATE 1 (1.00 g, 2.39 mmol) in CH$_2$Cl$_2$ (10 mL). After being stirred at room temperature overnight, the mixture was concentrated. The resulting residue was diluted with toluene (5 mL) then concentrated again. The resulting acid was used directly for the following step. LC5 1.21 min. (M+H)$^+$ 361.

A DMF solution (10 mL) of the product of the previous step (900 mg, 2.49 mmol), 5-(trifluoromethoxy)isoindole hydrochloride (507 mg, 2.49 mmol), EDC (669 mg, 3.49 mmol), HOBt (535 mg, 3.49 mmol) and Et$_3$N (1.73 mL, 12.5 mmol) was stirred at room temperature overnight. The solution was diluted with EtOAc then washed with water then brine. The organics were dried over Na$_2$SO$_4$, filtered, then concentrated to afford the title compound, which was used directly for the following step. LC5 1.41 min. (M+H)$^+$ 546.
Step B. 4-(1-{1-(4-Chlorophenyl)-2-oxo-2-[5-(trifluoromethoxy)-1,3-dihydro-2H-isoindol-2-yl]ethyl}butyl)benzoic acid

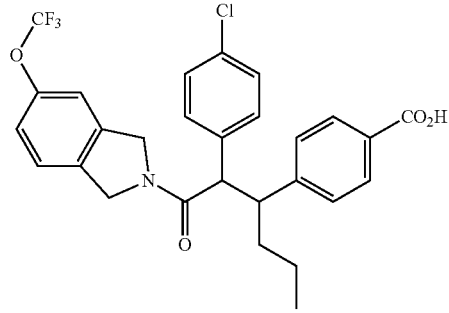

Sodium hydroxide (5.0 M in H$_2$O, 0.48 mL, 2.4 mmol) was added to a solution of the product from the previous step (1.30 g, 2.38 mmol) in methanol, then the mixture was stirred at room temperature overnight. The methanol was removed by concentration, then the mixture was diluted with water and 1N HCl (aq). The product was extracted into EtOAc. The organics were washed with water then brine, dried over Na$_2$SO$_4$, filtered, then concentrated to afford the title compound, which was used directly for the following step. LC5 1.34 min. (M+H)$^+$ 532.
Step C. N-[4-(1-{1-(4-Chlorophenyl)-2-[5-(2-methoxypyridin-3-yl)-1,3-dihydro-2H-isoindol-2-yl]-2-oxoethyl}butyl)benzoyl]-β-alanine

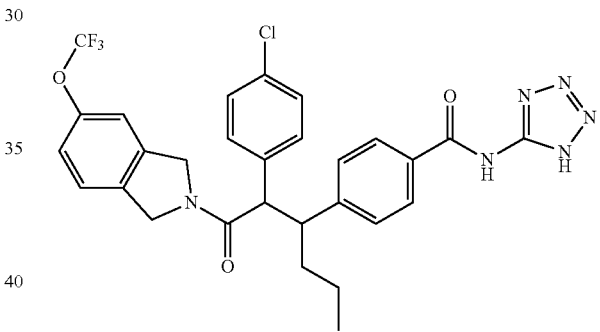

A solution of the product from the previous step (75 mg, 0.141 mmol), 5-amino-1H-tetrazole (14.4 mg, 0.169 mmol), EDC (40 mg, 0.21 mmol), HOBt (32 mg, 0.21 mmol) and Et$_3$N (0.10 mL, 0.71 mmol) in DMF (2 mL) was stirred at room temperature overnight. The solution was diluted with EtOAc then washed with water then brine. The organics were dried over anhydrous Na$_2$SO$_4$, filtered, then concentrated. The resulting residue was purified by reverse-phase HPLC to afford racemic mixtures of the two diastereomers of the title compound.

Minor isomer (faster-eluting on reverse-phase HPLC and less potent glucagon receptor antagonist): $^1$H NMR (600 MHz, DMSO-d$_6$): δ 12.22 (s, 1 H); 7.87 (d, J=7.9 Hz, 2 H); 7.43 (t, J=8.9 Hz, 1 H); 7.38-7.30 (m, 3 H); 7.30-7.22 (m, 3 H); 7.14-7.11 (m, 2 H); 5.34 (t, J=15.8 Hz, 1 H); 4.82-4.68 (m, 2 H); 4.58 (t, J=14.1 Hz, 1 H); 4.24 (dd, J=13.9, 11.1 Hz, 1 H); 3.48 (td, J=11.0, 3.5 Hz, 1 H); 1.73-1.63 (m, 2 H); 1.04-0.86 (m, 3 H); 0.74 (t, J=7.3 Hz, 3 H). LC4 1.34 min. (M+H)$^+$ 599.
Major isomer (slower-eluting on reverse-phase HPLC and more potent glucagon receptor antagonist): $^1$H NMR (600 MHz, DMSO-d$_6$): δ 12.26 (s, 1 H); 7.99 (d, J=7.9 Hz, 2 H); 7.60-7.52 (m, 6 H); 7.46-7.37 (m, 2 H); 7.36-7.17 (m, 1 H); 4.92 (t, J=15.2 Hz, 1 H); 4.62 (t, J=14.2 Hz, 1 H); 4.41-4.28 (m, 2 H); 4.24 (dd, J=16.6, 9.0 Hz, 1 H); 3.38 (td, J=11.0, 3.5

Hz, 1 H); 1.44-1.37 (m, 1 H); 1.11 (d, J=11.3 Hz, 1 H); 0.88-0.78 (m, 3 H); 0.60 (t, J=7.3 Hz, 3 H). LC4 1.34 min. (M+H)+ 598.

Using the chemistry described for the preparation of INTERMEDIATE 1 and in EXAMPLES 1-5, the compounds in TABLES 2, 4, and 5 were prepared as enantiopure compounds. The data listed are for the most active glucagon receptor antagonist among the four possible stereoisomers. Most compounds in TABLES 1, 3, and 6 were also prepared as single stereoisomers, with the data listed being those for the most active stereoisomer. The following examples, however, were prepared as racemic mixtures, and the data provided are those for the more active of the two diastereomers: 42-47, 57-59, 102-105. Additionally, the data provided for examples 99-101 are those obtained from a mixture of four stereoisomers—two sets of racemic diastereomers. The $R^1$ and $R^3$ groups that are shown in TABLES 1-6 are specified when they represent a value other than a hydrogen atom. The remaining $R^1$ and $R^3$ groups that are unspecified are hydrogen atoms.

TABLE 1

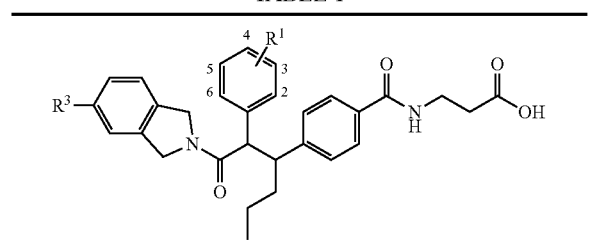

| EXAMPLE | $R^1$ | $R^3$ | LC-MS Data |
|---|---|---|---|
| 6 | 4-CF$_3$ | CF$_3$ | LC2 1.55 min. (M + H)+ 621 |
| 7 | 3-F, 5-F | CF$_3$ | LC2 1.37 min. (M + H)+ 589 |
| 8 | 4-CF$_3$ | 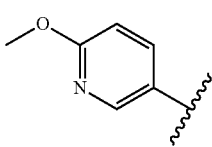 | LC2 1.23 min. (M + H)+ 660 |
| 9 | 3-F, 5-F | 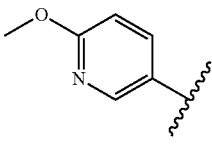 | LC2 1.38 min. (M + H)+ 628 |
| 10 | 4-Cl | F | LC4 2.27 min. (M + H)+ 537 |
| 11 | 4-Cl | 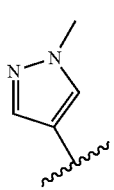 | LC2 1.58 min. (M + H)+ 599 |

TABLE 1-continued

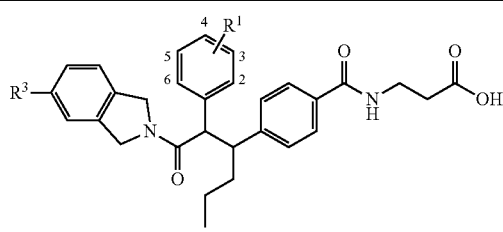

| EXAMPLE | $R^1$ | $R^3$ | LC-MS Data |
|---|---|---|---|
| 12 | 4-Cl | 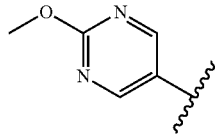 | LC2 1.39 min. (M + H)+ 627 |
| 13 | 4-Cl | 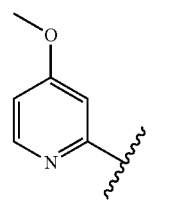 | LC2 1.22 min. (M + H)+ 626 |
| 14 | 4-Cl | OCF$_3$ | LC2 1.29 min. (M + H)+ 603 |
| 15 | 4-Cl | 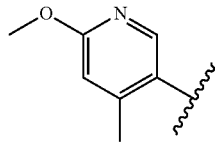 | LC2 1.37 min. (M + H)+ 640 |
| 16 | 4-Cl | 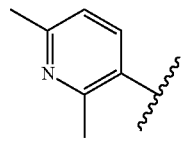 | LC2 1.27 min. (M + H)+ 624 |
| 17 | 4-Cl | OCH$_3$ | LC2 1.23 min. (M + H)+ 549 |
| 18 | 4-Cl | Cl | LC2 1.25 min. (M + H)+ 553 |
| 19 | 4-Cl | 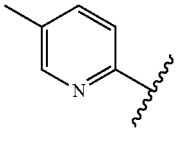 | LC2 1.13 min. (M + H)+ 610 |
| 20 | 4-Cl | 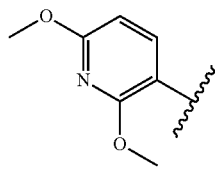 | LC2 1.36 min. (M + H)+ 656 |

TABLE 1-continued

| EXAMPLE | R¹ | R³ | LC-MS Data |
|---|---|---|---|
| 21 | 4-Cl | 6-methoxy-2-methylpyridin-3-yl | LC2 1.34 min. (M + H)⁺ 640 |
| 22 | 4-Cl | 5-(trifluoromethyl)pyridin-2-yl | LC2 1.20 min. (M + H)⁺ 664 |
| 23 | 4-Cl | 5-chloro-2-methoxypyridin-4-yl | LC2 1.27 min. (M + H)⁺ 660.6 |
| 24 | 4-Cl | 6-methylpyridin-3-yl | LC2 1.15 min. (M + H)⁺ 610.4 |
| 25 | 4-Cl | 4-methoxypyridin-3-yl | LC2 1.14 min. (M + H)⁺ 626 |
| 26 | 4-Cl | 2-methoxypyridin-4-yl | LC2 1.56 min. (M + H)⁺ 626 |
| 27 | 4-Cl | 3-fluoropyridin-4-yl | LC2 1.28 min. (M + H)⁺ 614 |
| 28 | 4-Cl | pyridin-3-yl | LC2 1.12 min. (M + H)⁺ 596 |
| 29 | 4-Cl | pyridin-2-yl | LC2 1.12 min. (M + H)⁺ 596.4 |
| 30 | 4-Cl | 2-methylpyridin-4-yl | LC2 1.27 min. (M + H)⁺ 610 |
| 31 | 4-Cl | 2-methoxypyridin-3-yl | LC2 1.43 min. (M + H)⁺ 626 |
| 32 | 4-Cl | pyridin-4-yl | LC2 1.12 min. (M + H)⁺ 596.4 |
| 33 | 4-Cl | pyrimidin-5-yl | LC2 1.35 min. (M + H)⁺ 597 |
| 34 | 4-Cl | H | LC2 3.58 min. (M + H)⁺ 517.6 |
| 35 | 4-Cl | CF₃ | LC2 1.25 min. (M + H)⁺ 587 |
| 36 | 4-Cl | CN | LC2 1.20 min. (M + H)⁺ 544 |
| 37 | 4-Cl | CH₃ | LC2 1.42 min. (M + H)⁺ 533 |
| 38 | 4-Cl | Br | LC2 1.45 min. (M + H)⁺ 599 |
| 39 | 4-Cl | 4-methylphenyl | LC2 1.51 min. (M + H)⁺ 609 |

TABLE 1-continued

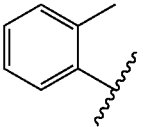

| EXAMPLE | R¹ | R³ | LC-MS Data |
|---|---|---|---|
| 40 | 4-Cl | 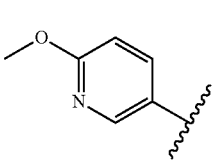 2-methylphenyl | LC2 1.29 min. (M + H)⁺ 609 |
| 41 | 4-Cl | 6-methoxypyridin-3-yl | LC2 1.22 min. (M + H)⁺ 626 |
| 42 | 4-Cl | 4-fluorophenyl | LC2 1.25 min. (M + H)⁺ 613 |
| 43 | 4-Cl | 4-chlorophenyl | LC2 1.28 min. (M + H)⁺ 629 |
| 44 | 4-Cl | 4-methoxyphenyl | LC2 1.25 min. (M + H)⁺ 625 |
| 45 | 4-Cl | 4-trifluoromethoxyphenyl | LC2 1.43 min. (M + H)⁺ 679 |
| 46 | 4-Cl | 4-trifluoromethylphenyl | LC2 1.42 min. (M + H)⁺ 663 |
| 47 | 4-Cl | 3-methylphenyl | LC2 1.41 min. (M + H)⁺ 609 |

TABLE 2

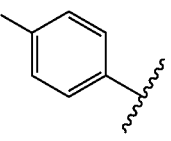

| EXAMPLE | R³ | LC-MS Data |
|---|---|---|
| 48 | 4-OCH₃ | LC2 1.24 min. (M + H)⁺ 549.4 |
| 49 | 4-CH₃ | LC2 1.25 min. (M + H)⁺ 533.4 |
| 50 | 4-CF₃ | LC2 1.27 min. (M + H)⁺ 587.4 |
| 51 | 4-Cl, 7-Cl | LC2 1.51 min. (M + H)⁺ 589 |
| 52 | 4-Cl, 5-Cl | LC2 1.30 min. (M + H)⁺ 587 |
| 53 | 4-Cl | LC2 1.23 min. (M + H)⁺ 553 |
| 54 | 5-Cl, 6-Cl | LC2 1.26 min. (M + H)⁺ 589 |
| 55 | 4-Cl, 6-Cl | LC2 1.26 min. (M + H)⁺ 587 |
| 56 | 4-F | LC4 2.20 min. (M + H)⁺ 537 |

TABLE 3

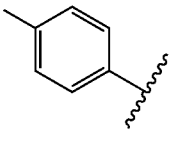

| EXAMPLE | R³ | LC-MS Data |
|---|---|---|
| 57 | 4-methoxyphenyl | LC2 1.52 min (M + H)⁺ 625.4 |
| 58 | 4-trifluoromethylphenyl | LC2 1.35 min (M + H)⁺ 663.4 |
| 59 | 4-chlorophenyl | LC2 1.55 min (M + H)⁺ 629.6 |
| 60 | CN | LC2 1.41 min. (M + H)⁺ 544 |
| 61 | CH₃ | LC2 1.44 min. (M + H)⁺ 533 |
| 62 | Br | LC2 1.47 min. (M + H)⁺ 599 |

TABLE 3-continued

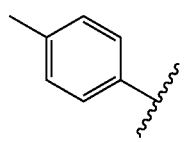

| EXAMPLE | R³ | LC-MS Data |
|---|---|---|
| 63 | 4-methylphenyl | LC2 1.55 min (M + H)⁺ 609 |

TABLE 4

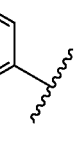

| EXAMPLE | R¹ | R³ | LC-MS Data |
|---|---|---|---|
| 64 | 4-CF₃ | CF₃ | LC2 1.24 min. (M + H)⁺ 635.4 |
| 65 | 3-F, 5-F | CF₃ | LC2 1.41 min. (M + H)⁺ 603 |
| 66 | 4-Cl | 6-methoxypyridin-3-yl | LC2 1.21 min. (M + H)⁺ 640.4 |
| 67 | 4-Cl | 2-methylphenyl | LC2 1.29 min. (M + H)⁺ 623.6 |
| 68 | 4-Cl | Cl | LC2 1.26 min. (M + H)⁺ 567 |

TABLE 4-continued

| EXAMPLE | R¹ | R³ | LC-MS Data |
|---|---|---|---|
| 69 | 4-Cl | 4-chlorophenyl | LC2 1.31 min. (M + H)⁺ 643.4 |
| 70 | 4-Cl | 4-methylphenyl | LC2 1.31 min. (M + H)⁺ 623.4 |
| 71 | 4-Cl | 4-(trifluoromethyl)phenyl | LC2 1.33 min. (M + H)⁺ 677.5 |
| 72 | 4-Cl | 4-chloro-2-methoxyphenyl | LC2 1.31 min. 673 |
| 73 | 4-Cl | 2-chloro-4-methylphenyl | LC2 1.51 min. (M + H)⁺ 657 |
| 74 | 4-Cl | 5-fluoro-2-methoxyphenyl | LC2 1.29 min. (M + H)⁺ 657.4 |

TABLE 4-continued

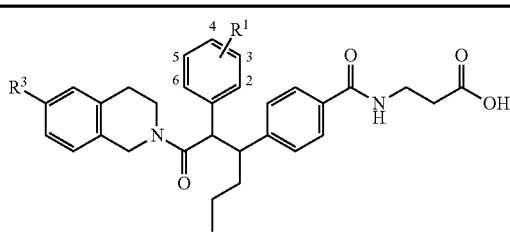

| EXAMPLE | R¹ | R³ | LC-MS Data |
|---|---|---|---|
| 75 | 4-Cl | 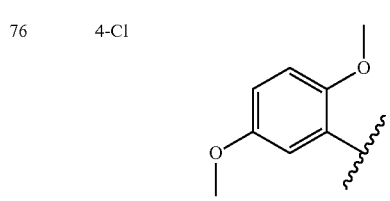 | LC2 1.30 min. (M + H)⁺ 645 |
| 76 | 4-Cl |  | LC2 1.28 min. (M + H)⁺ 669.4 |
| 77 | 4-Cl | 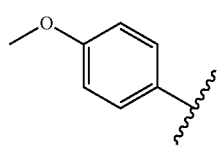 | LC2 1.33 min. (M + H)⁺ 641 |
| 78 | 4-Cl | | LC2 1.28 min. (M + H)⁺ 639.4 |
| 79 | 4-Cl | OCH₃ | LC2 1.39 min. (M + H)⁺ 563 |
| 80 | 4-Cl | CF₃ | LC2 1.44 min. (M + H)⁺ 601 |

TABLE 4-continued

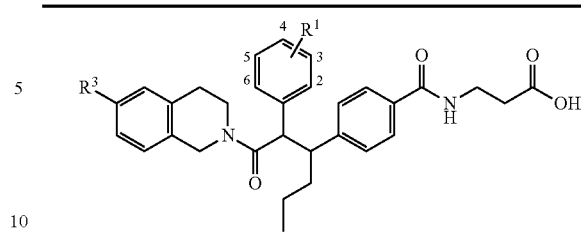

| EXAMPLE | R¹ | R³ | LC-MS Data |
|---|---|---|---|
| 81 | 4-Cl | CN | LC2 1.37 min. (M + H)⁺ 558 |
| 82 | 4-Cl | CH₃ | LC2 1.42 min. (M + H)⁺ 547 |
| 83 | 4-Cl | OCF₃ | LC2 1.26 min. (M + H)⁺ 617 |
| 84 | 4-Cl | SCH₃ | LC2 1.26 min. (M + H)⁺ 579 |
| 85 | 4-Cl | Br | LC2 1.27 min. (M + H)⁺ 613 |
| 86 | 4-Cl | F | LC1 2.38 min. (M + H)⁺ 549 |
| 87 | 4-Cl | H | LC3 3.70 min. (M + H)⁺ 531 |

TABLE 5

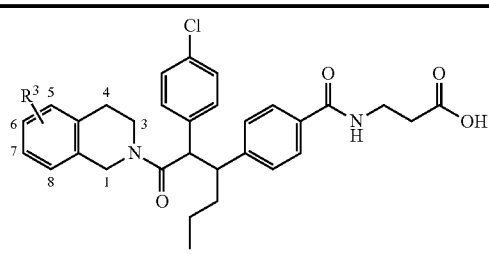

| EXAMPLE | R³ | LC-MS Data |
|---|---|---|
| 88 | 7-(4-CH₃—C₆H₄) | LC2 1.32 min. (M + H)⁺ 623.4 |
| 89 | 7-(4-Cl—C₆H₄) | LC2 1.35 min. (M + H)⁺ 643.4 |
| 90 | 7-(4-OCH₃—C₆H₄) | LC2 1.29 min. (M + H)⁺ 639.5 |
| 91 | 5-Cl | LC2 1.30 min. (M + H)⁺ 567 |
| 92 | 7-CH₃ | LC2 1.51 min. (M + H)⁺ 623 |
| 93 | 7-F | LC2 1.40 min. (M + H)⁺ 551 |
| 94 | 7-Cl | LC2 1.25 min. (M + H)⁺ 567 |
| 95 | 7-CF₃ | LC2 1.25 min. (M + H)⁺ 601 |
| 96 | 6-OCH₃, 7-OCH₃ | LC2 1.22 min. (M + H)⁺ 593.4 |
| 97 | 7-Br | LC2 1.27 min. (M + H)⁺ 613 |
| 98 | 7-Cl, 8-Cl | LC3 2.55 min. (M + H)⁺ 603 |

TABLE 6

[Structure: core compound with R³-substituted isoindoline-N-C(=O)-CH(4-chlorophenyl)-CH(propyl)-(4-C(=O)NH-Y-phenyl)]

| EXAMPLE | R³ | Y | LC-MS Data |
|---|---|---|---|
| 99 | OCF₃ | -CH₂-CH(OH)-COOH | LC4 1.29 min. (M + H)⁺ 619 |
| 100 | OCF₃ | -CH₂-CH(Me)-COOH | LC4 1.33 min. (M + H)⁺ 617 |
| 101 | OCF₃ | -CH(Me)-CH₂-COOH | LC4 1.33 min. (M + H)⁺ 617 |
| 102 | OCF₃ | -CH₂-CF₂-COOH | LC4 1.36 min. (M + H)⁺ 639 |
| 103 | OCF₃ | -CH₂-(1H-tetrazol-5-yl) | LC4 1.30 min. (M + H)⁺ 613 |
| 104 | OCF₃ | -CH₂CH₂-C(=O)NH₂ | LC4 1.31 min. (M + H)⁺ 602 |
| 105 | CH₃ | -CH₂CH₂-SO₃H | LC6 2.92 min. (M + H)⁺ 569 |
| 106 | Br | -CH₂CH₂-SO₃H | LC6 2.63 min. (M + H)⁺ 633 |
| 107 | CF₃ | -CH₂CH₂-SO₃H | LC6 2.67 min. (M + H)⁺ 623 |

TABLE 6-continued

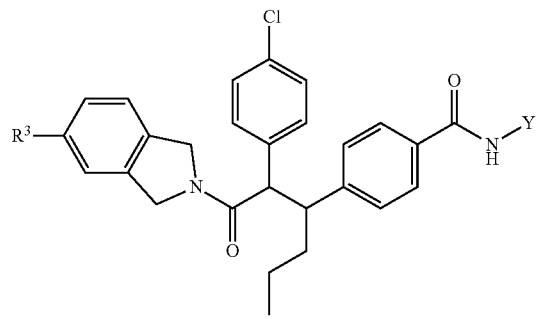

| EXAMPLE | R³ | Y | LC-MS Data |
|---|---|---|---|
| 108 | 4-methylphenyl | -CH₂CH₂-S(O)₂-OH | LC6 2.89 min. (M + H)⁺ 645 |
| 109 | 6-methoxypyridin-3-yl | -CH₂CH₂-S(O)₂-OH | LC6 2.61 min. (M + H)⁺ 662 |

BIOLOGICAL ASSAYS

The ability of the compounds of the present invention to inhibit the binding of glucagon and their utility in treating or preventing type 2 diabetes mellitus and the related conditions can be demonstrated by the following in vitro assays.

Glucagon Receptor Binding Assay

A stable CHO (Chinese hamster ovary) cell line expressing cloned human glucagon receptor was maintained as described (Chiechi, et. al. *J Biol Chem* 272, 7765-9(1997); Cascieri, et. al. *J Biol Chem* 274, 8694-7(1999)). To determine antagonistic binding affinity of compounds, 0.001-0.003 mg of cell membranes from these cells were pre-incubated with 0.100 mg WGA-coated PVT SPA beads (Amersham) for 20 minutes at room temperature in 25 µL of a buffer containing 50 mM Tris-HCl (pH 7.5), 5 mM MgCl₂, 2 mM EDTA, 0.1% BSA and 3% glycerol in Costar 384 well plates with clear bottoms (#3706). Next, 25 µL of $^{125}$I-Glucagon (New England Nuclear, MA) ($1\times10^{-14}$ mol per well) and either 1 µL solutions of test compounds or 0.001 mM unlabeled glucagon or DMSO were added and mixed. After 4-12 hours incubation at room temperature, the radioactivity bound to the cell membranes was determined in a radioactive emission detection counter (Wallac-Microbeta). Data were analyzed using the Data Analyzer software program of Merck & Co., Inc. The IC₅₀ values were calculated using non-linear regression analysis assuming single-site competition. IC₅₀ values for the compounds of the invention are generally in the range of as low as about 1 nM to as high as about 500 nM, and thus have utility as glucagon antagonists. The IC₅₀ values are shown below in TABLE 4 for the more active isomer of indicated compounds.

TABLE 4

| Example | IC₅₀ (nM) | Example | IC₅₀ (nM) | Example | IC₅₀ (nM) |
|---|---|---|---|---|---|
| 1 | 0.8 | 30 | 0.6 | 79 | 1.5 |
| 2 | 48 | 36 | 5.5 | 80 | 0.9 |
| 3 | 10 | 37 | 0.6 | 82 | 0.4 |
| 4 | 0.5 | 41 | 0.6 | 86 | 2.0 |
| 5 | 2.2 | 49 | 0.1 | 88 | 3.2 |
| 6 | 0.4 | 55 | 0.6 | 93 | 9.8 |
| 8 | 0.4 | 63 | 0.2 | 99 | 1.1 |
| 9 | 0.4 | 69 | 1.0 | 101 | 5.9 |
| 13 | 2.0 | 70 | 1.6 | 107 | 1.1 |

Inhibition of Glucagon-stimulated Intracellular cAMP Formation

Exponentially growing CHO cells expressing human glucagon receptor were harvested with the aid of enzyme-free dissociation media (Specialty Media), pelleted at low speed, and resuspended in the Cell Stimulation Buffer included in the Flash Plate cAMP kit (New England Nuclear, SMP0004A). The adenylate cyclase assay was conducted as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in the presence of compounds or DMSO controls for 30 minutes, then stimulated with glucagon (250 pM) for an additional 30 minutes. The cell stimulation was stopped by addition of equal amounts of a detection buffer containing lysis buffer as well as $^{125}$I-labeled cAMP tracer (NEN). After 3 hours of incubation at room temperature the bound radioactivity was determined in a liquid scintillation counter (Top-Count-Packard Instruments). Basal activity (100% inhibition) was determined using the DMSO control while 0% inhibition was defined at the amount of pmol cAMP produced by 250 pM glucagon. The resulting amount of cAMP generated per compound dose was back-calculated from a cAMP standard curve based on the percent inhibition achieved at each dose. The calculated cAMP levels were plotted versus compound dose to obtain IC$_{50}$ values using non-linear four-parameter curve fitting with Assay Data Analyzer software (Merck & Co., Inc.).

Certain embodiments of the invention have been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A compound represented by formula I:

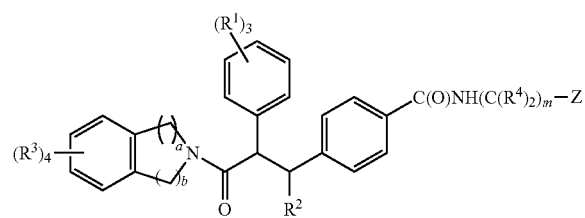

I or a pharmaceutically acceptable salt thereof wherein:
a is an integer selected from 1, 2 and 3, and b is an integer selected from 0 and 1, such that the sum of a and b is 2 or 3;
each R$^1$ represents H or is selected from the group consisting of: halo, CN, OH, NO$_2$, CO$_2$R$^a$, NR$^a$R$^b$, S(O)$_p$R$^a$, C$_{1-10}$alkyl, C$_{2-10}$alkenyl or C$_{1-10}$alkoxy, the alkyl and alkenyl portions of C$_{1-10}$alkyl, C$_{2-10}$alkenyl and C$_{1-10}$alkoxy being optionally substituted with 1-5 halo atoms; and further optionally substituted with 1 group selected from OH, oxo and C$_{1-6}$alkoxy;
p represents 0, 1 or 2;
each R$^a$ and R$^b$ independently represents H or C$_{1-4}$alkyl optionally substituted with 1-5 halo atoms; and further optionally substituted with 1 group selected from OH, oxo and C$_{1-6}$alkoxy;
R$^2$ represents C$_{1-6}$alkyl or C$_{2-6}$alkenyl, each optionally substituted with 1-5 halo atoms, and further optionally substituted with 1 group selected from OH, oxo and C$_{1-6}$alkoxy;
each R$^3$ represents H or halo, or 1-3 R$^3$ groups represent H or halo and the remainder represent a member selected from the group consisting of: CN; OH; NO$_2$; CO$_2$R$^a$; NR$^a$R$^b$; S(O)$_p$R$^a$; phenyl or 5-6 membered heteroaryl containing 1-3 nitrogen atoms and 0-1 oxygen or sulfur atom, said phenyl and heteroaryl being optionally substituted with 1-3 halo atoms and 1-2 members selected from the group consisting of: C$_{1-3}$alkyl, C$_{1-3}$alkoxy, haloC$_{1-3}$alkyl and haloC$_{1-3}$alkoxy; C$_{1-10}$alkyl; C$_{2-10}$alkenyl and C$_{1-10}$alkoxy, the alkyl and alkenyl portions of C$_{1-10}$alkyl, C$_{2-10}$alkenyl and C$_{1-10}$alkoxy being optionally substituted with 1-5 halo atoms; and further optionally substituted with 1 group selected from OH, oxo, NR$^a$R$^b$, and C$_{1-6}$alkoxy;
each R$^4$ independently represents H or is selected from the group consisting of: halo, OH, C$_{1-4}$alkyl, OC$_{1-4}$alkyl, haloC$_{1-4}$alkyl and haloOC$_{1-4}$alkyl;
m represents 0, 1 or 2; when m represents 0, Z represents tetrazolyl;
when m represents 1, Z represents a member selected from the group consisting of: CO$_2$H, SO$_3$H, C(O)NH$_2$ and tetrazolyl; and when m represents 2, Z represents a member selected from the group consisting of: CO$_2$H, SO$_3$H and C(O)NH$_2$.

2. A compound in accordance with claim 1 or a pharmaceutically acceptable salt thereof wherein each R$^1$ represents H or is selected from the group consisting of: halo, CN, C$_{1-6}$alkyl, C$_{1-6}$alkoxy, haloC$_{1-6}$alkyl and haloC$_{1-6}$alkoxy.

3. A compound in accordance with claim 2 or a pharmaceutically acceptable salt thereof wherein each R$^1$ represents H or is selected from the group consisting of: halo selected from fluoro and chloro; CN; CH$_3$; OCH$_3$; CF$_3$ and OCF$_3$.

4. A compound in accordance with claim 3 or a pharmaceutically acceptable salt thereof wherein each R$^1$ represents H, halo selected from fluoro and chloro; CN; CH$_3$; or CF$_3$.

5. A compound in accordance with claim 1 or a pharmaceutically acceptable salt thereof wherein R$^2$ represents a member selected from the group consisting of: C$_{1-6}$alkyl and C$_{3-4}$alkenyl, each optionally substituted with 1-3 halo atoms.

6. A compound in accordance with claim 5 or a pharmaceutically acceptable salt thereof wherein R$^2$ represents C$_{2-5}$alkyl optionally substituted with 1-3 halo atoms.

7. A compound in accordance with claim 6 or a pharmaceutically acceptable salt thereof wherein R$^2$ represents n-propyl, optionally substituted with 1-3 halo atoms selected from fluoro and chloro.

8. A compound in accordance with claim 1 or a pharmaceutically acceptable salt thereof wherein each R$^3$ represents H or halo, or 1-3 R$^3$ groups represent H or halo and the remainder represent a member selected from the group consisting of: CN; OH; CO$_2$R$^a$; NR$^a$R$^b$; S(O)$_p$R$^a$ ; phenyl or 5-6 membered heteroaryl containing 1-2 nitrogen atoms, said phenyl and heteroaryl being optionally substituted with 1-3 halo atoms and 1-2 members selected from the group consisting of: C$_{1-3}$alkyl, C$_{1-3}$alkoxy, haloC$_{1-3}$alkyl and haloC$_{1-3}$alkoxy; C$_{1-6}$alkyl and C$_{1-6}$alkoxy, the alkyl portions of C$_{1-6}$alkyl and C$_{1-6}$alkoxy being optionally substituted with 1-5 halo atoms.

9. A compound in accordance with claim 8 or a pharmaceutically acceptable salt thereof wherein each R$^3$ represents H or halo selected from fluoro, chloro and bromo, or 1-3 R$^3$ groups represent H or halo selected from fluoro, chloro and bromo, and the remainder represent a member selected from the group consisting of: CN; S(O)$_p$R$^a$; phenyl or 5-6 membered heteroaryl selected from the group consisting of: pyrazolyl, imidazolyl, pyridyl, pyrimidinyl and pyrazinyl, said phenyl and heteroaryl being optionally substituted with 1-3 fluoro or chloro atoms and 1-2 members selected from the group consisting of: C$_{1-3}$alkyl, C$_{1-3}$alkoxy, haloC$_{1-3}$alkyl and haloC$_{1-3}$alkoxy; C$_{1-3}$alkyl and C$_{1-3}$alkoxy, the alkyl portions of C$_{1-3}$alkyl and C$_{1-3}$alkoxy being optionally substituted with 1-3 fluoro or chloro atoms.

10. A compound in accordance with claim 1 or a pharmaceutically acceptable salt thereof wherein each R$^4$ represents H, halo selected from F and Cl, OH, C$_{1-2}$alkyl, C$_{1-2}$alkoxy, haloC$_{1-2}$alkyl and haloC$_{1-2}$alkoxy wherein the halo portion of haloC$_{1-2}$alkyl and haloC$_{1-2}$alkoxy is selected from F and Cl.

11. A compound in accordance with claim 10 or a pharmaceutically acceptable salt thereof wherein each R$^4$ represents H, F, Cl, OH and CH$_3$.

12. A compound in accordance with claim 11 or a pharmaceutically acceptable salt thereof wherein each R$^4$ represents H, F, CH$_3$ or OH.

13. A compound in accordance with claim 1 represented by formula I:

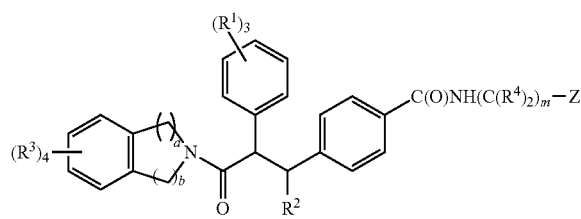

or a pharmaceutically acceptable salt thereof wherein:
a represents 1 or 2, and b represents 1, such that the sum of a and b is 2 or 3;
each $R^1$ represents H or is selected from the group consisting of: halo, CN, $C_{1-6}$alkyl, $C_{1-6}$alkoxy, halo$C_{1-6}$alkyl and halo$C_{1-6}$alkoxy;
$R^2$ represents a member selected from the group consisting of: $C_{1-6}$alkyl and $C_{3-4}$alkenyl, each optionally substituted with 1-3 halo atoms;
each $R^3$ represents H or halo, or 1-3 $R^3$ groups represent H or halo and the remainder represent a member selected from the group consisting of: CN; OH; $CO_2R^a$; $NR^aR^b$; $S(O)_pR^a$; phenyl or 5-6 membered heteroaryl containing 1-2 nitrogen atoms, said phenyl and heteroaryl being optionally substituted with 1-3 halo atoms and 1-2 members selected from the group consisting of: $C_{1-3}$alkyl, $C_{1-3}$alkoxy, halo$C_{1-3}$alkyl and halo$C_{1-3}$alkoxy; $C_{1-6}$alkyl and $C_{1-6}$alkoxy, the alkyl portions of $C_{1-6}$alkyl and $C_{1-6}$alkoxy being optionally substituted with 1-5 halo atoms;
each $R^4$ represents H, halo selected from F and Cl, OH, $C_{1-2}$alkyl, $C_{1-2}$alkoxy, halo$C_{1-2}$alkyl and halo$C_{1-2}$alkoxy wherein the halo portion of halo$C_{1-2}$alkyl and halo$C_{1-2}$alkoxy is selected from F and Cl;
m represents 0 or 1 and Z represents tetrazolyl, or m is 1 or 2 and Z represents $CO_2H$, $SO_3H$ or $C(O)NH_2$.

14. A compound in accordance with claim 1 or a pharmaceutically acceptable salt thereof, selected from the following tables:

EXAMPLE 1

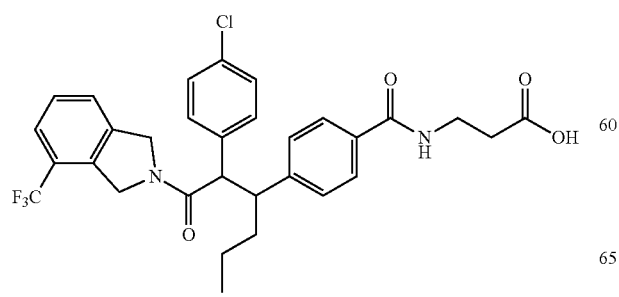

EXAMPLE 2

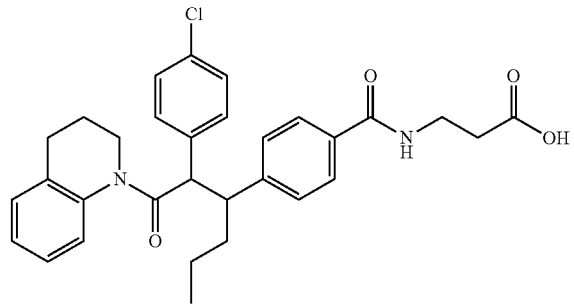

EXAMPLE 3

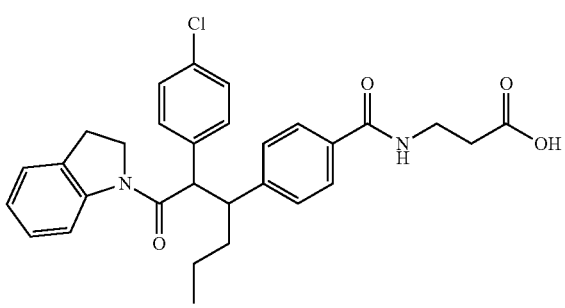

EXAMPLE 4

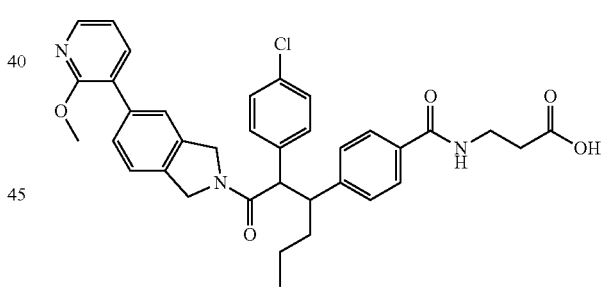

EXAMPLE 5

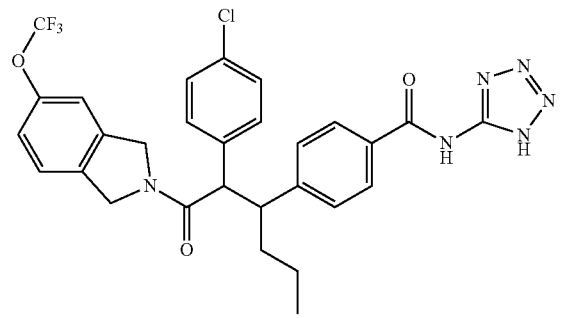

TABLE 1

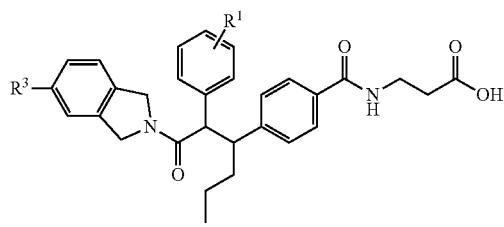

| EXAMPLE | R¹ | R³ |
|---|---|---|
| 6 | 4-CF₃ | CF₃ |
| 7 | 3-F, 5-F | CF₃ |
| 8 | 4-CF₃ | 6-methoxypyridin-3-yl |
| 9 | 3-F, 5-F | 6-methoxypyridin-3-yl |
| 10 | 4-Cl | F |
| 11 | 4-Cl | 1-methyl-1H-pyrazol-4-yl |
| 12 | 4-Cl | 2-methoxypyrimidin-5-yl |
| 13 | 4-Cl | 4-methoxypyridin-2-yl |
| 14 | 4-Cl | OCF₃ |
| 15 | 4-Cl | 6-methoxy-4-methylpyridin-3-yl |
| 16 | 4-Cl | 2,6-dimethylpyridin-3-yl |
| 17 | 4-Cl | OCH₃ |
| 18 | 4-Cl | Cl |

TABLE 1-continued

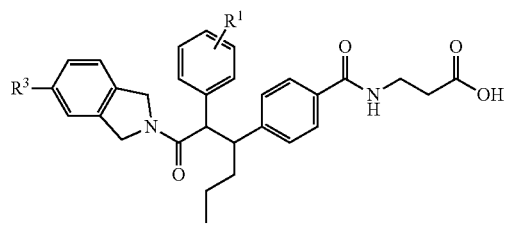

| EXAMPLE | R¹ | R³ |
|---|---|---|
| 19 | 4-Cl | 5-methylpyridin-2-yl |
| 20 | 4-Cl | 2,6-dimethoxypyridin-3-yl |
| 21 | 4-Cl | 6-methoxy-2-methylpyridin-3-yl |
| 22 | 4-Cl | 5-trifluoromethylpyridin-2-yl |
| 23 | 4-Cl | 5-chloro-2-methoxypyridin-4-yl |
| 24 | 4-Cl | 6-methylpyridin-3-yl |
| 25 | 4-Cl | 4-methoxypyridin-3-yl |
| 26 | 4-Cl | 2-methoxypyridin-4-yl |
| 27 | 4-Cl | 3-fluoropyridin-4-yl |

TABLE 1-continued

Structure (Examples 28-40):
R³-substituted isoindoline-N-C(=O)-CH(Ar-R¹)-CH(propyl)-C₆H₄-C(=O)-NH-CH₂-CH₂-COOH

| EXAMPLE | R¹ | R³ |
|---|---|---|
| 28 | 4-Cl | pyridin-3-yl |
| 29 | 4-Cl | pyridin-2-yl |
| 30 | 4-Cl | 2-methylpyridin-4-yl |
| 31 | 4-Cl | 2-methoxypyridin-3-yl |
| 32 | 4-Cl | pyridin-4-yl |
| 33 | 4-Cl | pyrimidin-5-yl |
| 34 | 4-Cl | H |
| 35 | 4-Cl | CF₃ |
| 36 | 4-Cl | CN |
| 37 | 4-Cl | CH₃ |
| 38 | 4-Cl | Br |
| 39 | 4-Cl | 4-methylphenyl |
| 40 | 4-Cl | 2-methylphenyl |

TABLE 1-continued

Structure (Examples 41-47): same scaffold

| EXAMPLE | R¹ | R³ |
|---|---|---|
| 41 | 4-Cl | 6-methoxypyridin-3-yl |
| 42 | 4-Cl | 4-fluorophenyl |
| 43 | 4-Cl | 4-chlorophenyl |
| 44 | 4-Cl | 4-methoxyphenyl |
| 45 | 4-Cl | 4-(trifluoromethoxy)phenyl |
| 46 | 4-Cl | 4-(trifluoromethyl)phenyl |
| 47 | 4-Cl | 3-methylphenyl |

TABLE 2
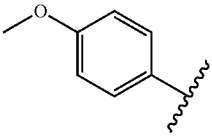
| EXAMPLE | R³ |
|---|---|
| 48 | 4-OCH₃ |
| 49 | 4-CH₃ |
| 50 | 4-CF₃ |
| 51 | 4-Cl, 7-Cl |
| 52 | 4-Cl, 5-Cl |
| 53 | 4-Cl |
| 54 | 5-Cl, 6-Cl |
| 55 | 4-Cl, 6-Cl |
| 56 | 4-F |
TABLE 3
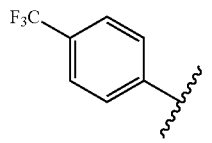
| EXAMPLE | R³ |
|---|---|
| 57 | 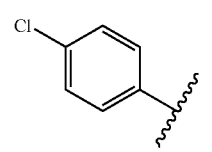 |
| 58 | 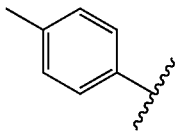 |
| 59 | 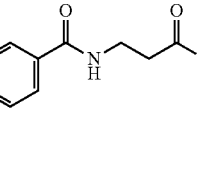 |
| 60 | CN |
| 61 | CH₃ |
| 62 | Br |
| 63 | 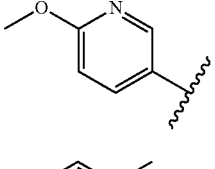 |
TABLE 4
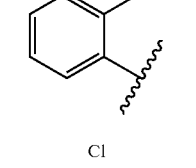
| EXAMPLE | R¹ | R³ |
|---|---|---|
| 64 | 4-CF₃ | CF₃ |
| 65 | 3-F, 5-F | CF₃ |
| 66 | 4-Cl | 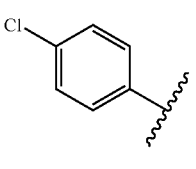 |
| 67 | 4-Cl | 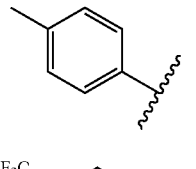 |
| 68 | 4-Cl | Cl |
| 69 | 4-Cl | 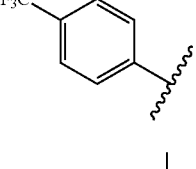 |
| 70 | 4-Cl | 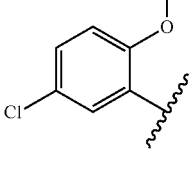 |
| 71 | 4-Cl | 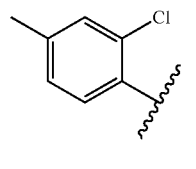 |
| 72 | 4-Cl | 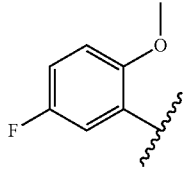 |
| 73 | 4-Cl |  |
| 74 | 4-Cl |  |

TABLE 4-continued

[Structure: tetrahydroisoquinoline with R³, substituted phenyl with R¹, benzamide-NH-CH2CH2-COOH, with propyl chain]

| EXAMPLE | R¹ | R³ |
|---|---|---|
| 75 | 4-Cl | 2,4-difluorophenyl |
| 76 | 4-Cl | 2,5-dimethoxyphenyl |
| 77 | 4-Cl | 2-fluoro-4-methylphenyl |
| 78 | 4-Cl | 4-methoxyphenyl |
| 79 | 4-Cl | OCH₃ |
| 80 | 4-Cl | CF₃ |
| 81 | 4-Cl | CN |
| 82 | 4-Cl | CH₃ |
| 83 | 4-Cl | OCF₃ |
| 84 | 4-Cl | SCH₃ |
| 85 | 4-Cl | Br |
| 86 | 4-Cl | F |
| 87 | 4-Cl | H |

TABLE 5

[Structure: tetrahydroisoquinoline with R³, 4-chlorophenyl, benzamide-NH-CH2CH2-COOH, propyl chain]

| EXAMPLE | R³ |
|---|---|
| 88 | 7-(4-CH₃—C₆H₄) |
| 89 | 7-(4-Cl—C₆H₄) |
| 90 | 7-(4-OCH₃—C₆H₄) |
| 91 | 5-Cl |
| 92 | 7-CH₃ |

TABLE 5-continued

| EXAMPLE | R³ |
|---|---|
| 93 | 7-F |
| 94 | 7-Cl |
| 95 | 7-CF₃ |
| 96 | 6-OCH₃, 7-OCH₃ |
| 97 | 7-Br |
| 98 | 7-Cl, 8-Cl |

TABLE 6

[Structure: isoindoline with R³, 4-chlorophenyl, benzamide-NH-Y, propyl chain]

| EXAMPLE | R³ | Y |
|---|---|---|
| 99 | OCF₃ | -CH₂-CH(OH)-COOH |
| 100 | OCF₃ | -CH₂-CH(Me)-COOH |
| 101 | OCF₃ | -CH₂-CH(Me)-CH₂-COOH (Me at β) |
| 102 | OCF₃ | -CH₂-CF₂-COOH |
| 103 | OCF₃ | -CH₂-(1H-tetrazol-5-yl) |

TABLE 6-continued

[Structure: isoindoline with R³ substituent, N-acyl group bearing a 4-chlorophenyl and a CH(propyl) attached to 4-(C(=O)NH-Y)phenyl]

| EXAMPLE | R³ | Y |
|---|---|---|
| 104 | OCF₃ | -CH₂CH₂C(=O)NH₂ |
| 105 | CH₃ | -CH₂CH₂CH₂S(=O)₂OH |
| 106 | Br | -CH₂CH₂CH₂S(=O)₂OH |
| 107 | CF₃ | -CH₂CH₂CH₂S(=O)₂OH |
| 108 | 4-methylphenyl | -CH₂CH₂CH₂S(=O)₂OH |
| 109 | 6-methoxypyridin-3-yl | -CH₂CH₂CH₂S(=O)₂OH |

15. A pharmaceutical composition comprising a compound in accordance with claim 1 or a pharmaceutically acceptable salt thereof in combination with a pharmaceutically acceptable carrier.

16. A pharmaceutical composition in accordance with claim 15 further comprised of a member selected from the group consisting of: simvastatin, mevastatin, ezetimibe, atorvastatin, metformin, sibutramine, orlistat, Qnexa, topiramate, naltrexone, bupriopion, phentermine, losartan, hydrochlorothiazide, buformin, phenformin, troglitazone, pioglitazone, rosiglitazone, insulin, somatostatin, voglibose, miglitol, acarbose, sitagliptin, vildagliptin, saxagliptin, alogliptin, acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide, repaglinide, rimonabant and taranabant.

* * * * *